United States Patent

Sagae et al.

[11] Patent Number: 5,834,404
[45] Date of Patent: Nov. 10, 1998

[54] SUBSTITUTED BICYCLOHEPTANEDIONE DERIVATIVE AND HERBICIDE

[75] Inventors: Takahiro Sagae; Masao Yamaguchi; Hiroyuki Adachi, all of Kanagawa, Japan; Kazuyuki Tomida, Halstead, N.Y.; Akihiro Takahashi; Takashi Kawana, both of Kanagawa, Japan

[73] Assignee: Nippon Soda Co., ltd., Tokyo, Japan

[21] Appl. No.: 836,285

[22] PCT Filed: Nov. 7, 1995

[86] PCT No.: PCT/JP95/02259

§ 371 Date: Jul. 15, 1997

§ 102(e) Date: Jul. 15, 1997

[87] PCT Pub. No.: WO96/14285

PCT Pub. Date: May 17, 1996

[30] Foreign Application Priority Data

Nov. 7, 1994 [JP] Japan ..................... 6-297854
Jun. 23, 1995 [JP] Japan ..................... 7-180961

[51] Int. Cl.$^6$ .................. A01N 31/04; A01N 43/36; C07C 49/115; C07D 211/70
[52] U.S. Cl. ............. 504/348; 504/244; 504/310; 504/313; 504/314; 568/327; 568/374; 558/426; 558/428; 560/53; 560/119; 546/314
[58] Field of Search ............... 504/348, 244, 504/310, 313, 314; 568/327, 374; 558/426, 428; 560/53, 119; 546/314

[56] References Cited

U.S. PATENT DOCUMENTS

| 5,006,158 | 4/1991 | Carter et al. | 558/396 |
| 5,092,919 | 3/1992 | Nguyen | 568/329 |
| 5,094,685 | 3/1992 | Baba et al. | 568/31 |
| 5,114,461 | 5/1992 | Geach et al. | 568/306 |
| 5,228,898 | 7/1993 | Ueda et al. | 504/348 |

*Primary Examiner*—Deborah C. Lambkin
*Attorney, Agent, or Firm*—Jacobson, Price, Holman & Stern, PLLC

[57] ABSTRACT

The present invention is directed to substituted bicycloheptanedion e derivatives represented by a general formula [I];

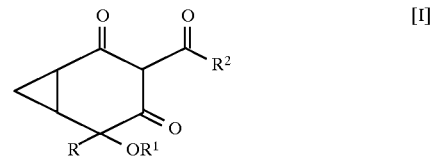

wherein R represents $C_1$–$C_4$ alkyl, $R^1$ represents hydrogen, $C_1$–$C_{10}$ alkyl, $C_2$–$C_4$ alkenyl, $C_2$–$C_4$ alkynyl, aralkyl, $C_2$–$C_4$ haloalkynyl, $C_1$–$C_4$ alkoxy $C_1$–$C_4$ alkyl, $C_1$–$C_4$ haloalkyl, $C_2$–$C_4$ haloalkenyl, etc. and $R^2$ represents optionally substituted phenyl or optionally substituted pyridyl, the salts thereof and herbicides comprising the same as the active ingredient.

11 Claims, No Drawings

SUBSTITUTED BICYCLOHEPTANEDIONE DERIVATIVE AND HERBICIDE

This application is a 371 of PCT/JP95/02249 filed Nov. 07, 1995.

FIELD OF THE INVENTION

The present invention is related to novel bicycloheptanedione derivatives and a herbicide.

BACKGROUND ART

Substituted bicycloheptanedione derivatives similar to the compounds according to the present invention and herbicides comprising such derivative are disclosed in Japanese Patent Laid-opened No. Hei 3-255047.

DISCLOSURE OF THE INVENTION

It is an object of the present invention to provide a herbicide which can be advantageously manufactured in an industrial scale, assures firm herbicidal efficacy with a lower dose and high safeness, and possesses a better selectivity in the herbicidal activity between crops and weeds.

The present invention is directed to substituted bicycloheptanedion e derivatives represented by a general formula [I];

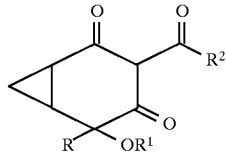

wherein R represents $C_1$–$C_4$ alkyl, $R^1$ represents hydrogen, $C_1$–$C_{10}$ alkyl in either straight or branched chain, $C_2$–$C_4$ alkenyl, aralkyl, $C_2$–$C_4$ haloalkenyl, $C_1$–$C_4$ alkoxy $C_1$–$C_4$ alkyl, $C_1$–$C_4$ haloalkyl, $C_2$–$C_4$ haloalkenyl, hydroxy $C_1$–$C_4$ alkyl, —A—$C_3$–$C_4$ alkyl, —A—$C_3$–$C_6$ cycloalkyl, —A—C(O)r, —A—$CH_2CN$ or phenyl, A represents a single bond or $C_1$–$C_4$ alkylene, r represents hydrogen, $C_1$–$C_4$ alkyl $C_1$–$C_4$ alkoxy or phenyl, and $R^2$ represents optionally substituted phenyl or optionally substituted pyridyl, or the salts thereof, herbicides, and intermediates represented by a general formula [II];

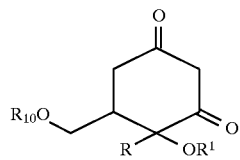

wherein R and $R^1$ are as described above and $R^{10}$ is $C_1$–$C_4$ alkyl, aralkyl or acetyl.

In the general formula [I] described above, as examples of the $C_1$–$C_{10}$ alkyl in either straight or branched chain represented by $R^1$, methyl, ethyl, propyl, isopropyl, butyl, sec-butyl, t-butyl, pentyl, neopentyl, hexyl, heptyl, octyl, nonyl, decyl and so on can be given.

As examples of the $C_2$–$C_4$ alkenyl, vinyl, allyl, crotyl and the like can be given.

As examples of the $C_2$–$C_4$ alkylnyl, ethynyl, propargyl and the like can be given.

As examples of the aralkyl, benzyl, α-methylbenzyl, α, α-dimethylbenzyl, 2-phenylethyl, of those which benzene ring may be substituted with any of lower alkyls, halogen atoms, lower alkoxy, nitro, etc., and the like can be given.

As examples of the $C_2$–$C_4$ haloalkynyl, iodopropargyl and the like can be given.

As examples of the $C_1$–$C_4$ alkoxy $C_1$–$C_4$ alkyl, methoxymethyl, methoxyethyl, methoxypropyl, methoxyisopropyl, ethoxymethyl, ethoxyethyL, ethoxypropyl, propoxymethyl, propoxyethyl, propoxypropyl, butoxymethyl, butoxyethyl, isopropoxymethyl, isobutoxymethyl, butoxyethyl, t-butoxymethyl, butoxyethyl and the like can be given.

As examples of the $C_1$–$C_4$ haloalkyl, trifluoromethyl, trifluoroethyl, trichloromethyl, pentafluoroethyl, tribromomethyl and the like can be given.

As examples of the $C_2$–$C_4$ haloalkenyl, chlorovinyl, 3-chloroallyl, 3-chloroallyl, 2,3-dichloroallyl, 1-chloroallyl, 3-chlorocrotonyl and the like can be given.

As examples of the hydroxy $C_1$–$C_4$ alkyl, hydroxymethyl, hydroxyethyl, hydroxypropyl, hydroxybutyl, hydroxyisopropyl and the like can be given.

And, A of —A—$C_3$–$C_6$ cycloalkyl, —A—C(O)r and —A—$CH_2CN$ described above is a single bond or $C_1$–$C_4$ alkylene, such as methylene, ethylene and trimethylene, and wherein r represents hydrogen, $C_1$–$C_4$ alkyl, $C_1$–$C_4$ alkoxy or phenyl. Further, as examples of the $C_3$–$C_6$ cycloalkyl, cyclopropyl, cyclobutyl, cyclopentyl, cyclohexyl and the like can be given.

As example of the substituent to phenyl and pyridyl represented by $R^2$ in the general formula [I] described above, an halogen atom, such as fluorine, chlorine, bromine and iodine, $OR^5$ wherein $R^5$ is $C_1$–$C_4$ alkyl, such as methyl, ethyl, propyl, isopropyl, butyl, isobutyl and t-butyl, $C_2$–$C_4$ alkenyl, such as vinyl, 1-propenyl, 2-propenyl, isopropenyl, 1-butenyl, 2-butenyl and 3-butenyl, $C_2$–$C_4$ alkynyl, such as ethynyl and propargyl, $C_1$–$C_4$ haloalkyl, such as chloromethyl, dichloromethyl, trichloromethyl, difluoromethyl, trifluoromethyl, bromomethyl, dibromomethyl, chloroethyl, fluoroethyl, dichloroethyl, difluoroethyl, trifluoroethyl, tetrafluoromethyl, perfluoroethyl, chloropropyl, fluoropropyl, perfluoropropyl, chloroisopropyl, fluoroisopropyl, perfluoroisopropyl, chlorobutyl, fluorobutyl, perfluorobutyl, chloroisobutyl, fluoroisobutyl, perfluoroisobutyl, chloro-s-butyl, fluoro-s-butyl, perfluoro-s-butyl, chloro-t-butyl, fluoro-t-butyl and perfluoro-t-butyl, $C_1$–$C_4$ haloalkenyl, such as chlorovinyl fluorovinyl, chloroallyl, fluoroallyl, dichloroallyl, difluoroallyl, trichloroallyl, trifluoroallyl, bromoallyl, chloroisopropenyl, fluoroisopropenyl, chlorocrotyl, fluorocrotyl, dichlorocrotyl, difluorocrotyl, trichlorocrotyl and trifluorocrotyl, phenyl, halophenyl, $C_1$–$C_4$ alkoxy-substituted phenyl, phenyl $C_1$–$C_4$ alkyl, halophenyl $C_1$–$C_4$ alkyl, $C_1$–$C_4$ alkoxy-substituted phenyl $C_1$–$C_4$ alkyl, $C_1$–$C_4$ alkylthio $C_1$–$C_4$ alkyl, $C_1$–$C_4$ alkylsulfonyl $C_1$–$C_4$ alkyl, $C_1$–$C_4$ alkoxy $C_1$–$C_4$ alkyl, alkoxy $C_1$–$C_4$ alkoxy $C_1$–$C_4$ alkyl, $C_1$–$C_4$ alkoxycarbonyl $C_1$–$C_4$ alkyl, carboxy $C_1$–$C_4$ alkyl, cyano $C_1$–$C_4$ alkyl, $C_1$–$C_4$ alkylcarbonyl $C_1$–$C_4$ alkyl, $C_3$–$C_6$ cycloalkyl $C_1$–$C_4$ alkyl, provided that the cycloalkyl may contain 1 to 2 oxygen atoms, $C_1$–$C_5$ alkyl in either straight or branched chain, such as methyl, ethyl, propyl, isopropyl, butyl, isobutyl, sec-butyl, t-butyl, pentyl, isoamyl and neopentyl, $C_2$–$C_4$ alkenyl in either straight or branched chain, such as vinyl, 1-propenyl, 2-propenyl, isopropenyl, 1-butenyl, 2-butenyl and 3-butenyl, $C_2$–$C_4$ alkynyl, such as ethynyl, propargyl and butynyl, $C_1$–$C_4$ haloalkyl in either straight or branched chain, such as chloromethyl, dichloromethyl, trichloromethyl, difluoromethyl, trifluoromethyl, bromomethyl, dibromomethyl, chloroethyl, fluroethyl, dichloroethyl, difluoroethyl, trifluoroethyl, tetrafluoroethyl, perfluoroethyl, chloropropyl, fluoropropyl, perfluoropropyl, chloroisopropyl, fluoroisopropyl, perfluoroisopropyl, chlorobutyl, fluorobutyl, perfluorobutyl, chloroisobutyl, fluoroisobutyl, perfluoroisobutyl, chloro-s-butyl, fluoro-s-butyl, perfluoro-s-butyl, chloro-t-butyl, fluoro-t-butyl and perfluoro-t-butyl, $C_1$–$C_4$ haloalkenyl in either straight or branched chain, such as chlorovinyl, fluorovinyl, chloroallyl, fluoroallyl, dichloroallyl, difluoroallyl, trichloroallyl, trifluoroallyl, bromoallyl, chloroisopropenyl, fluoroisopropenyl, chlorocrotyl, fluorocrotyl, dichlorocrotyl, difluorocrotyl, trichlorocrotyl and trifluorocrotyl, $C_1$–$C_4$ alkoxy $C_1$–$C_4$ alkyl, such as methoxymethyl, methoxyethyl, methoxypropyl, methoxyisopropyl, methoxybutyl, ethoxymethyl, ethoxyethyl, ethoxypropyl, ethoxyisopropyl, ethoxybutyl, butoxymethyl, butoxyethyl, butoxypropyl, butoxyisopropyl and butoxybutyl, $C_1$–$C_4$ alkylthio $C_1$–$C_4$ alkyl, such as methylthiomethyl, methylthioethyl, methylthiopropyl, methylthioisopropyl, methylthiobutyl, ethylthiomethyl, ethylthioethyl, ethylthiopropyl, ethylthioisopropyl, ethylthiobutyl, propylthiomethyl, propylthioethyl, propylthiopropyl, propylthioisopropyl, propylthiobutyl, isopropylthiomethyl, isopropylthioethyl, isopropylthiopropyl, isopropylthioisopropyl, isopropylthiobutyl, butylthiomethyl, butylthioethyl, butylthiopropyl, butylthioisopropyl and butylthiobutyl, $C_1$–$C_4$ alkylsulfonyl $C_1$–$C_4$ alkyl, such as methylsulfonylmethyl, methylsulfonylethyl, methylsulfonylpropyl, methylsulfonylisopropyl, methylsulfonylbutyl, ethylsulfonylmethyl, ethylsulfonylethyl, ethylsulfonylpropyl, ethylsulfonylisopropyl, ethylsulfonylbutyl, propylsulfonylmethyl, propylsulfonylethyl, propylsulforylpropyl, propylsulfonylisopropyl, propylsulfonylbutyl, isopropylsulfonylmethyl, isopropylsulfonylethyl, isopropylsulfonylpropyl, isopropylsulfonylisopropyl, isopropylsulfonylbutyl, butylsulfonylmethyl, butylsulfonylethyl, butylsulfonylpropyl, butylsulfonylisopropyl and butylsulfonylbutyl, $C_1$–$C_4$ alkylsulfinyl $C_1$–$C_4$ alkyl, such as methylsulfinylmethyl, methylsulfinylethyl, methylsulfinylpropyl, methylsulfinylisopropyl, methylsulfinylbutyl, ethylsulfinylmethyl, ethylsulfinylethyl, ethylsulfinylpropyl, ethylsulfinylisopropyl, ethylsulfinylbutyl, propylsulfinylmethyl, propylsulfinylethyl, propylsulfinylpropyl, propylsulfinylisopropyl, propylsulfinylbutyl, isopropylsulfinylmethyl, isopropylsulfinylethyl, isopropylsulfinylpropyl, isopropylsulfinylisopropyl, isopropylsulfinylbutyl, butylsulfinylmethyl, buthylsulfinylethyl, butylsulfinylpropyl, butylsulfinylisopropyl and butylsulfinylbutyl, $S(O)_m R^6$, wherein $R^6$ represents $C_1$–$C_4$ alkyl, $C_2$–$C_4$ alkenyl, $C_2$–$C_4$ alkynyl, $C_1$–$C_4$ haloalkyl, $C_2$–$C_4$ haloalkenyl, phenyl, halophenyl, benzyl, halobenzyl, $C_1$–$C_4$ alkylthio $C_1$–$C_4$ alkyl, $C_1$–$C_4$ alkylsulfonyl $C_1$–$C_4$ alkyl, $C_1$–$C_4$ alkoxy $C_1$–$C_4$ alkyl, $C_1$–$C_4$ alkoxy $C_1$–$C_4$ alkoxy $C_1$–$C_4$ alkyl, $C_1$–$C_4$ alkoxycarbonyl $C_1$–$C_4$ alkyl, carboxy $C_1$–$C_4$ alkyl, cyano $C_1$–$C_4$ alkyl or $C_1$–$C_4$ alkylcarbonyl $C_1$–$C_4$ alkyl, and m represents 0, 1 or 2, nitro, aminosulfonyl, $C_1$–$C_4$ dialkylaminosulfonyl, such as dimethylaminosulfonyl, methylethylaminosulfonyl, methylproplaminosulfonyl, methylisopropylaminosulfonyl, methylbutylaminosulfonyl, methylisobutylaminosulfonyl, methyl-t-butylamincsulfonyl, diethylaminosulfonyl, ethylpropylaminosulfonyl, ethylisopropylaminosulfonyl, ethylbutylaminosulfonyl, ethylisobutylaminosulfonyl, ethyl-s-butylaminosulfonyl, ethyl-t-butylaminosulfonyl, dipropylaminosulfonyl, propylisopropylaminosulfonyl, propylbutylaminosulfonyl, propylisobutylaminosulfonyl, propyl-t-butylaminosulfonyl, diisopropylaminosulfonyl, isopropylbutylaminosulfonyl, isopropylisobutylaminosulfonyl, isopropyl-t-butylaminosulfonyl, dibutylaminosulfonyl, butylisobutylaminosulfonyl, butyl-t-butylaminosulfonyl and di-t-butylaminosulfonyl, $C_1$–$C_4$ alkoxycarbonyl, such as methoxycarbonyl, ethonycarbonyl, propoxycarbonyl, isopropoxycarbonyl, butoxycarbonyl, isobutoxycarbonyl, s-butoxycarbonyl and t-butoxycarbonyl, $C_1$–$C_4$ alkylcarbonyl, such as acetyl, propionyl, propylcarbonyl, isopropylcarbonyl, butylcarbonyl, isobutylcarbonyl, s-butylcarbonyl and t-butylcarbonyl, $CONR^{14}R^{15}$ wherein $R^{14}$ and $R^{15}$ are each independently hydrogen or $C_1$–$C_4$ alkyl, carboxyl, hydroxy, cyano, $NR^7R^8$ wherein $R^7$ and $R^8$ are each independently hydrogen, $C_1$–$C_4$ alkyl, $C_1$–$C_4$ alkoxy $C_1$–$C_4$ alkyl, $C_1$–$C_4$ alkoxy, $C_1$–$C_4$ alkytcarbonyl, $C_1$–$C_4$ alkoxycarbonyl or $C_1$–$C_4$ alkylsulfonyl, or pyridyloxy optionally substituted with an halogen atom, $C_1$–$C_4$ alkyl or $C_1$–$C_4$ haloalkyl, and the phenyl may be substituted with from 1 to 5 substituents, whereas the pyridyl may be substituted with from 1 to 4 substituents, which substituents may be the same or different from one another when phenyl and pyridyl are substituted with more than 2 substituents, respectively.

Further, as examples of the group represented by $R^2$, 2,4-di-substituted phenyl, 2,3,4-tri-substituted phenyl, 5-substituted-pyridyl-2-yl, 5,6-di-substituted-pyridyl-2-yl, 2,6-di-substituted-pyridyl-3-yl, 4,6-di-substituted-pyridyl-3-yl and the like can be given.

As more preferable examples of groups represented by $R^2$, 2,4-dichlorophenyl, 2-nitro-4-chlorophenyl, 2-nitro-4-methanesulfonytphenyl, 2-chloro-4-methanesulfonylphenyl, 2-nitro-4-trifluoromethylphenyl, 2-chloro-4-trifluoromethylphenyl, 2-nitro-4-cyanophenyl, 2-methyl-4-trifluoromethylphenyl, 2-methyl-4-methanesulfonylphenyl, 2-trifluoromethyl-4-chlorophenyl, 2-trifluoromethyl-4-methanesufonyiphenyl, 2,4-bistrifluoromethylphenyl, 2,4-bis-methanesulfonylphenyl, 2,3,4-trichlorophenyl, 2,3-dichloro-4-methanesulfonylmethylpheniyl, 2,3-dichloro-4- trifluoromethylphenyl, 2,3-dimethyl-4-methanesulfonylphenyl, 2,3-dimethyl-4-trifluoromethylphenyl, 2,3-dimethyl-4-chloropnenyl, 2-chloro-3-methyl-4-methanesulfonylphenyl, 2-chloro-3-methoxy-4-methanesulfonylphenyl, 2-chloro-3-difluoromethoxy-4-methanesulfonylphenyl, 2-chloro-3-trifluoromethoxy-4-methanesulfonylphenyl, 2-chloro-3-trifluoromethyl-4-methanesulfonylphenyl, 2,4-dichloro-3-methoxyphenyl, 2-methyl-3-methoxy-4-chlorophenyl, 2-methyl-3-methoxy-4-methanesulfonylphenyl, 2-trifluoromethyl-3-methoxy-4-methainesulfonylphenyl, 2,4-bis-trifluoromethyl-3-methoxyphenyl, 2-trifluoromethyl-3-methyl-4-methanesulfonylphenyl, 2,4-bis-trifluoromethyl-3-methylphenyl, 2-methyl-3-difluoromethoxy-4-chlorophenyl, 2-methyl-3-difluoromethoxy-4-methanesulfonylphenyl, 2,4,6-tris-trifluoromethylphenyl, 2-methyl-3-halo-4-methanesulfonyl, 2-methyl-6-methanesulfonyl-pyridine-3-yl, 2-trifluoromethyl-6-methanesulfonyl-pyridine-3-yl, 2-chloro-6-methanesulfonyl-pyridine-3-yl, and the like can be given.

(Manufacturing of compounds)

The compounds according to the present invention can be manufactured according to a method represented by the following reaction formula.
(Manufacturing method-1)

metal carbonates, tri($C_1$–$C_6$ alkyl)amines, pyridines, sodium phosphate and the like can be given as examples, and as examples of the solvent to be used in the same reaction, water, methylene chloride, chloroform, toluene, ethyl acetate, N, N-dimethylformamide, THF, dimethoxy ethane, acetonitrile and the like can be given.

The mixture prepared for the reaction is continuously stirred at a temperature of from 0° to 50° C. until completion of the reaction. Alternatively, the compounds represented by [IVa] and [IVb] are obtainable from a reaction in a two-phase system with using a phase-transfer agent, such as a quaternized ammonium salt.

A compound represented by [IVa] and a compound represented by [IVb] are also obtainable from a reaction of a compound represented by [II] and a compound represented by a general formula $R^2COOH$ [III'], which is one of the compound represented by [III] and in which Z is hydrogen, in the presence of a condensing agent, such as DCC. As a solvent to be used in the reaction with DCC as described above, methylene chloride, chloroform, benzene, toluene, ethyl acetate, N, N-dimethylformamide, THF, dimethoxy ethane, acetonitrile, etc. can be used. The mixture prepared for the reaction is stirred at a temperature of from −10° to 50° C. until completion of the reaction, and the reacted-product is prepared pursuant to a customary post-reaction procedure.

In the reaction formula described above, the rearrangement reaction to a compound represented by [V] is pro-

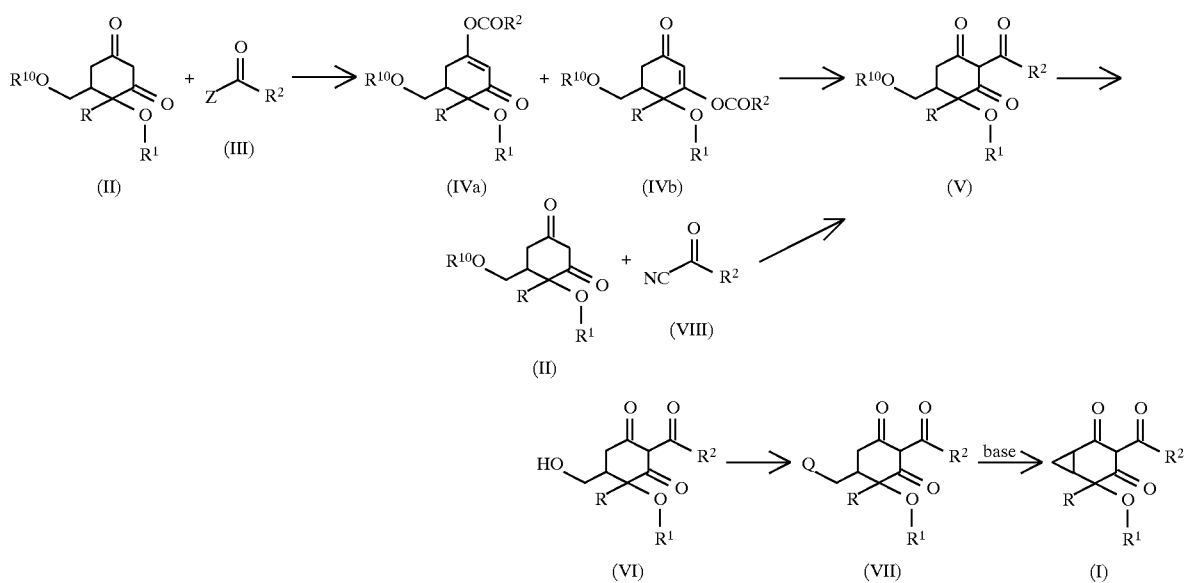

In the reaction formula described hereinabove, a compound represented by a general formula [IVa] and a compound represented by a general formula [IVb] can be obtained by allowing a compound represented by [II] in an amount of 1 mol, wherein $R^{10}$ represents $C_1$–$C_4$ alkyl, aralkyl or acetyl, to a reaction with a compound represented by [III] in an amount of 1 mol, wherein Z represents an halogen atom, alkylcarbonyloxy, alkoxycarbonyloxy or benzoyloxy, in the presence of a base in an excess amount, provided that either the compound represented by [II] or the compound represented by [III] in an excess amount may be used, alternatively.

As the base to be used in the above reaction, alkali metal hydroxides, such as KOH and NaOH, alkali metal carbonates, alkaline earth metal hydroxides, alkaline earth ceeded in the presence of a cyano compound and a mild base. For example, a compound represented by [IVa] in an amount of 1 mol and a compound represented by [IVb] in an amount of 1 mol are allowed to a reaction in the presence of said base in an amount of from 1 to 4 mol, and more preferably from 1 to 2 mol, and said cyano compound in an amount of from 0.01 to 0.5 mol or more, and more preferably from 0.05 to 0.2 mol.

As the base to be used in the reaction described above, any of the bases given above can be used.

Also, as the cyano compound described above, potassium cyanide, sodium cyanide, acetone cyanohydrin, hydrogen cyanide, a polymer supporting potassium cyanide, etc. can be used. In addition, by using a phase transfer agent, such as crown ether, time required to accomplish the reaction can be shortened.

And temperature appropriate for the reaction described above is in a range lower than 80° C., and more preferably in a range of from 20° to 40° C.

As the solvent to be used in the reaction described above, 1,2-dichloro ethane, toluene, acetonitrile, methylene chloride, ethyl acetate, N,N-dimethylformamide, methyl-isobutyl ketone, THF, dimethoxy ethane, etc. can be given as the example.

The compound represented by a general formula [V] is also obtainable according to a method as described hereinbelow by allowing a compound represented by [II] and a compound represented by [VIII] to a reaction in the presence of a base, and as well as in the presence of a lewis acid, if necessary.

The base to be used in the method is an alkali metal hydroxide, such as KOH and NaOH, an alkaline earth metal hydroxide, a tri($C_1$–$C_6$ alkyl)amine, pyridine, sodium carbonate, sodium phosphate or the like. As examples of the appropriate lewis acid, zinc chloride, aluminium trichloride and the like are given. The reaction is proceeded in an organic solvent, such as acetonitrile and methylene chloride, at an appropriate temperature in a range of from –20° C. to a boiling point of said solvent. It is preferable to use a base and zinc chloride, if the use of the latter is appropriate, both in a slightly excess amount to that of the compound represented by [II].

The compound represented by [VI] is manufactured by allowing a compound represented by [V] to any of a reaction with a hydrohalogenic acid, such as hydrochloric acid and hydrobromic acid, trifluoroacetic acid, boron tribromide or the like, hydrogenolysis, hydrolysis with an alkali and so on, and by allowing the reacted-product subsequently to hydrolysis, if appropriate.

The compound represented by [VI] is derived to a compound represented by [VII], wherein Q is a detaching group such as an halogen atom, alkylsulfonyloxy and arylsulfonyloxy, via any reaction of halogenation, alkylsulfonato formation, and arylsulfonato formation, etc. pursuant to a customarily-known method. By allowing the compound represented by [VII] to the said reactions for 30 minutes to several ten hours in a solvent and in the presence of a base in an amount more than 1 mol at a temperature of from –20° C. to a boiling point of the solvent used, and more preferably from an ambient temperature to 100° C., a compound represented by [I] can be manufactured.

As examples of the base described above, alkali metal hydroxides, such as KOH and NaOH, alkaline earth metal hydroxides, tri($C_1$–$C_6$ alkyl) amines, pyridine, DBU, t-BuOK, triton B, sodium carbonate, sodium phosphate and the like are given, and as examples of the solvent, water, alcohols, methylene chloride, benzene, toluene, ethyl acetate, N, N-dimethylformamide, THF, dimethoxy ethane, acetonitrile, etc. can be used either alone or mixtures thereof.

The substituted benzoic acid chloride and substituted benzoic acid described above can be manufactured according to a customarily-known method.

Cyclic dione compounds represented by a general formula [II] can be manufactured according to a reaction formula as shown hereinbelow.

Manufacturing method of dione compounds

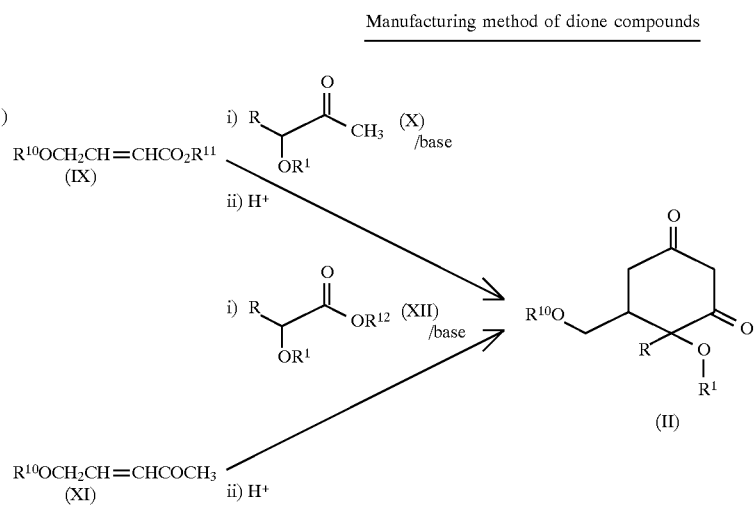

-continued
Manufacturing method of dione compounds

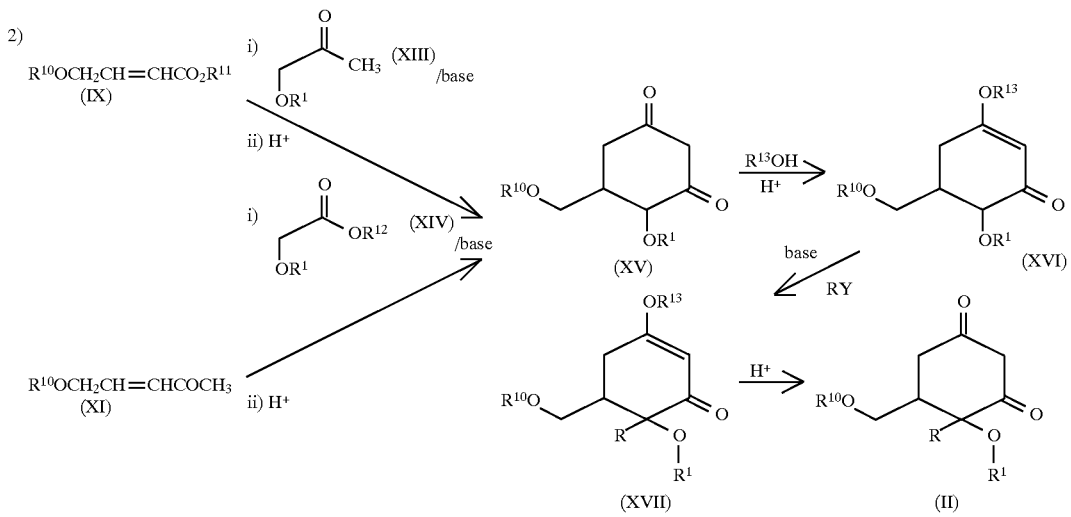

For example, dione compounds represented by a general formula [II] in the reaction formula described above can be manufactured by firstly allowing an unsaturated ester compound represented by a general formula [IX], wherein $R^{10}$ is as described above and $R^{11}$ represents $C_1$–$C_6$ alkyl, and a compound represented by a general formula [X], wherein $R^1$ is as described above, to a reaction in a solvent for 1 to several ten hours at a temperature of from −78° C. to a boiling point of said solvent in the presence of a base and subsequently neutralizing the reacted-product with an acid, such as hydrochloric acid. As the solvent to use in the above reaction, any of alcohols, THF, N, N-dimethylformamide, toluene, etc. can be used, whereas alkali metal alkoxides, sodium hydride, alkyl lithium, lithium diisopropylamide, etc. can be used as the said base.

Similarly, the dione compounds represented by the general formula [II] can be also manufactured in a reaction of a compound represented by [XI] and a compound represented by [XII], wherein $R^1$ is as described above and $R^{12}$ represents $C_1$–$C_6$ alkyl.

In addition, according to the same method as described above, a dione compound represented by [XV] is manufactured in both reactions of a compound represented by [IX] and a compound represented by [XIII], wherein $R^1$ is as described above, and a compound represented by [XI] and a compound represented by [XIV], wherein $R^1$ and $R^{12}$ are as described above, and the said dione compound obtained can be further converted to its enol ether form represented by a general formula [XVI] in a lower alcohol represented by a formula, $R^{13}$OH, in the presence of paratoluenesulfonic acid, etc. pursuant to a customarily-known method. Following thereto, by allowing the said enol ether form represented by [XVI] to a reaction with an alkylating agent, such as halogenated $C_1$–$C_4$ alkyl and $C_1$–$C_4$ alkylsulfuric acid, in a solvent for several to several ten hours at a temperature of from −78° C. to a boiling point of the solvent in the presence of a base and subsequently treating the reacted-product with an acid, such as hydrochloric acid, a dione compound represented by the general formula [II] can be also manufactured.

(Manufacturing method-2)

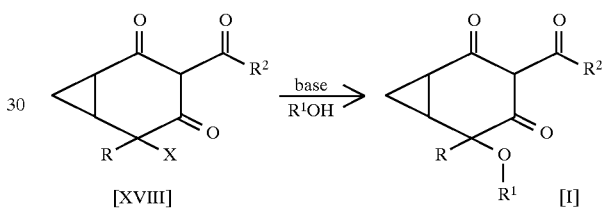

The compounds according to the present invention represented by a general formula [I] is manufactured by allowing a trione compound represented by a general formula [XVIII], wherein a cyclohexane ring being halogenated, to a reaction with an alcohol represented by a general formula, $R^1$OH, wherein $R^1$ is as described above, in a solvent at an appropriate temperature in a range of from −10° C. to a boiling point of the solvent in the presence of a base. As examples of the base used in the above reaction, alkali metal carbonates, such as $NaHCO_3$ and $K_2CO_3$, alkali metal carboxylates, such as sodium acetate, tri($C_1$–$C_6$)amines, silver salts, such as silver carbonate, silver oxide, phosphates and the like are given, whereas as the solvent used in the same reaction, $R^1$OH, methylene chloride, benzene, ethyl acetate, THF, acetonitrile, dimethoxy ethane, formamide, etc. can be used either alone or in a form of the mixture thereof. The halogenated trione compound represented by [XVIII] used in this reaction can be manufactured according to the method described hereinbelow.

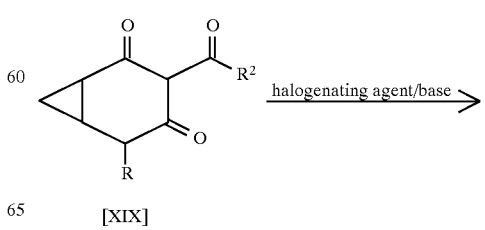

-continued

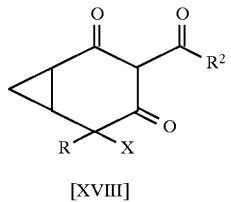

[XVIII]

Alternatively, the halogenated trione compound represented by a general formula [XVIII] can be manufactured by allowing a trione compound represented by a general formula [XIX] prepared according to a publicly-known method to a reaction with an halogenating agent, such as phenyltrimethyl ammonium tribromide, bromine and merdoramic acid dibromide, in a solvent for several to several tens hours at a temperature of from 0° C. to a boiling point of the solvent, and more preferably from an ambient temperature to 50° C., and in the presence of either a base or an acid, such as hydrobromic acid, if appropriate. As example of the solvent used in the reaction, methylene chloride, benzene, ethyl acetate, THF, acetonitrile, dimethoxy ethane and the like can be given.

(Manufacturing method-3)

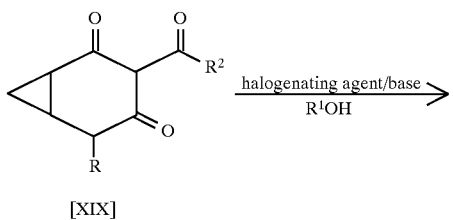

[XIX]

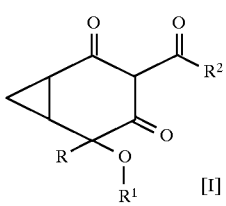

[I]

The compounds according to the present invention represented by a general formula [I] are also manufactured by allowing a trione compound represented by a general formula [XIX], which is prepared pursuant to a publicly-known method, to a reaction with both an alcohol having a general formula of $R^1OH$ and an halogenating agent, such as phenyltrimethyl ammonium tribromide, in a solvent for several to several tens hours at an appropriate temperature in a range of from 0° C. to a boiling point of the solvent, and more preferably from an ambient temperature to 50° C. and in the presence of a base. The solvents usable in the reaction are as described above.

All of raw materials represented by a general formulas [II], [V], [VI], [VII], [XV], [XVIII], and [XIX] contain several types of optically active substances, respectively, and the compounds according to the present invention represented by a general formula [I] also contain their optically active substances, respectively, and such optically active substances further exist in forms of various types of tautomers as represented in the following illustration, respectively. It should be noted that all types of these tautomers are fallen within a scope of the present invention.

Types of tautomers

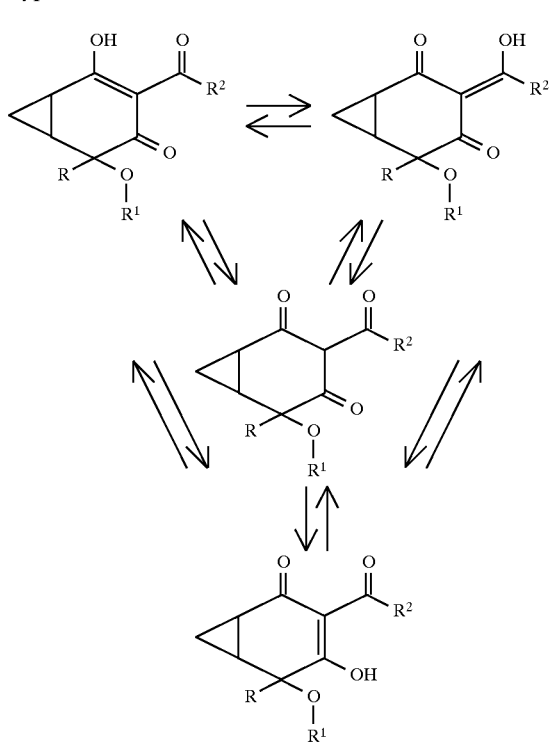

When the compounds represented by a general formula [I] contain a free hydroxy group, respectively, the salts thereof, particularly the salts agriculturally- and horticulturally-acceptable, the enamine form and its analogs, acylates, sulfonates, carbamates, ethers, thio ethers, sulfoxides and sulfones of such compounds can be derived therefrom. As appropriate examples of the salts being agriculturally- and horticulturally-acceptable, sodium salts, potassium salts, calcium salts and ammonium salts of the compounds are given.

As examples of the ammonium salts, salts formed with an ion represented by a general formula, $N^+R^aR^bR^cR^d$ wherein $R^a$, $R^b$, $R^c$ and $R^d$ are each independently hydrogen or any one selected from $C_1$–$C_{10}$ alkyls each substituted with hydroxy or the else when appropriate, can be given. When any of $R^a$, $R^b$, $R^c$ and $R^d$ is substituted alkyl, it is preferable that all of $R^a$, $R^b$, $R^c$ and $R^d$ contain 1 to 4 carbon atoms therein, respectively.

The appropriate enamine and the analog thereof are defined as a compound in which enol form hydroxy groups (at a part of —OH) are converted to a group represented by a general formula, —N $R^eR^f$ wherein $R^e$ and $R^f$ are each independently hydrogen or either alkyl or aryl, for example, phenyl, those which contain 1 to 6 carbon atoms and are substituted depending on the situation, to an halogen atom or to a group represented by a general formula, $S(O)_g$ $R^h$ wherein $R^h$ is either alkyl or aryl, for example, phenyl, which contains 1 to 6 carbon atoms and are substituted depending on the situation, and g represents 0, 1 or 2.

The appropriate acylates, ethers or carbamate derivatives are defined as compounds in which enol form hydroxy groups (at a part of —OH) are converted to any of groups represented by general formulas, —$OCOR^i$, —$OR^j$ and —$OCONR^kR^l$ wherein $R^i$ and $R^j$ are same as $R^h$ described above, and $R^k$ and $R^l$ are same as $R^e$ described above. These derivatives can be prepared according to a method customarily-known, and the objective compounds are obtainable after allowing them to an ordinary post-reaction procedure.

Structural formulas of the compounds according to the present invention were determined on the basis of analytical results obtained by using IR, NMR, MS, etc.

Best Mode for Carrying Out the Invention

Now, the present invention is further explained in detail with referring to Examples described below.

(EXAMPLE 1)

Manufacturing of 5-ethoxy-3-(3-methoxy-2-methyl-4-methylsulfonylbenzoyl) -5-methylbicyclo[4,1,0]heptane-2,4-dione (cis-form)

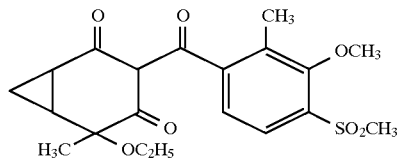

(1) Manufacturing of 4-ethoxy-5-methoxymethyl-4-methylcyclohexane-1,3-dione

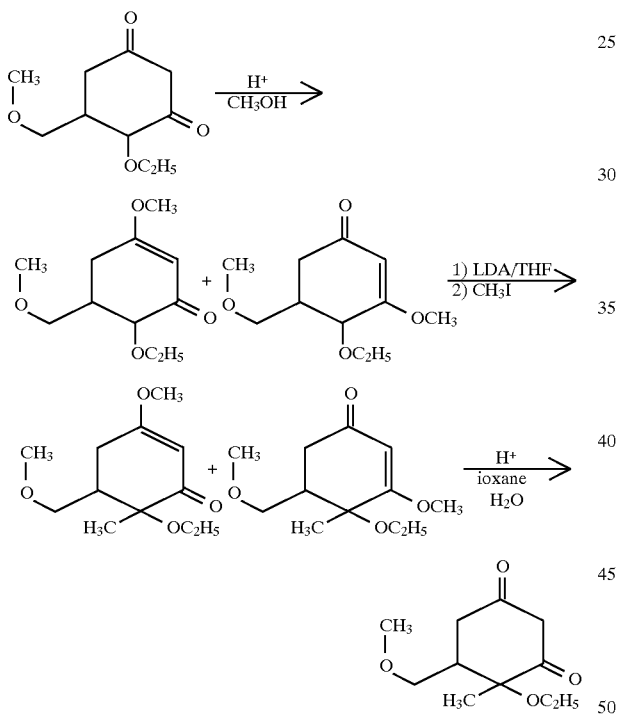

4-ethoxy-5-methoxymethylcyclohexane-1, 3-dione in an amount of 12.0 g (60.0 mmol) was dissolved in methanol in a volume of 150 ml, and sulfuric acid in a catalystic amount was then added to the solution. After stirring the solution for 2 hours, the solvent was removed from the solution by distillation under reduced pressure, and the solution remained was added with diluted hydrochloric acid to adjust it to acidic condition and was then extracted with methylene chloride. The organic solvent layer resulted was washed with saturated saline solution and dried with magnesium sulfate, then the solvent was removed by distillation therefrom. The crude product obtained was separated by means of silica gel column chromatography, where a mixture of ethyl acetate and n-hexane at a combining ratio of 1 to 1 is used, to obtain a compound containing both the 1-methyl enol ether form and the 3-methyl enol ether form in total amount of 7.8 g. The yield was 61%, and the physical state of the mixture was liquid having a high viscosity.

The obtained methyl enol ether form in an amount of 7.8 g (36.4 mmol) was dissolved in anhydrous tetrahydrofuran in a volume of 80 ml, and the solution was then fed dropwise slowly with lithium diisopropylamide in an amount of 2.2 equivalents, which consists of 18 ml diisopropylamine, 50 ml n-butyl lithium and 50 ml anhydrous tetrahydrofuran, at −70° C. After stirring the mixture for 30minutes, the mixture was added with iodomethane in a volume of 5.8 ml (93.2 mmol) and was subsequently taken out of a cooling bath and followed by stirring further for 1 hour. The reacted-solution was added with water and diluted hydrochloric acid to adjust it to acidic condition and then extracted with methylene chloride. The organic solvent layer resulted was washed with saturated saline solution and dried with magnesium sulfate, and the solvent remained was removed by distillation. A crude product was separated by means of silica gel column chromatography, where a mixture of ethyl acetate and n-hexane at a combining ratio of 1 to 1 is used, to obtaine a methylated product in an amount of 3.79 g. The yield was 46%, and the product was in liquid state having a high viscosity.

4-ethoxy-1-methoxy-5-methoxymethyl-4-methyl-1-cyclohexene-3-one in an amount of 3.79 g (16.6 mmol) was dissolved in a mixed-solvent consisting of 1,4-dioxane in a volume of 20 ml and diluted hydrochloric acid in a volume of 10 ml, and the solution was then stirred for 15 hours at an ambient temperature. The solvent used was removed by distillation under reduced pressure, then the remained was added with methylene chloride to proceed an extraction. The organic solvent layer resulted was washed with saturated saline solution and dried with magnesium sulfate, and the solvent remained was removed by distillation, thereby affording a viscous liquid product in an amount of 3.55 g. The yield was 99%.

(2) Manufacturing of 4-ethoxy-5-methoxymethyl-2-(3-methoxy-2-methyl-4-methylsulfonylbenzoyl)-4-methylcyclohexane-1,3-dione

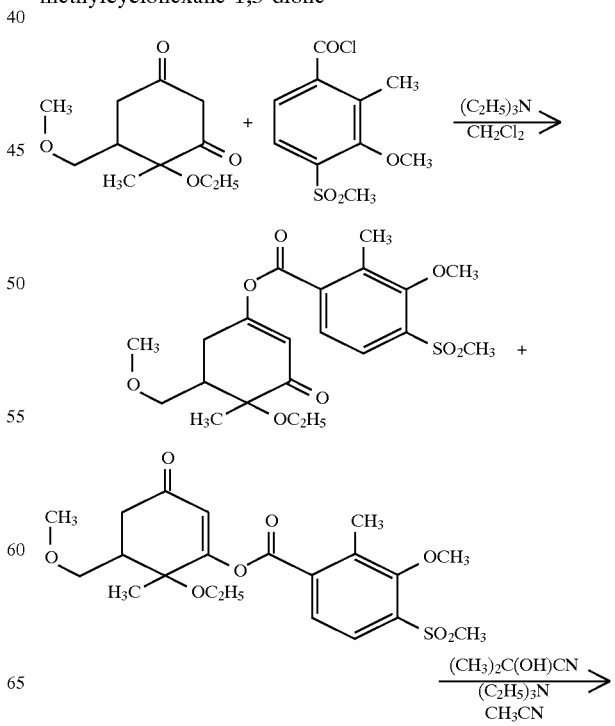

-continued

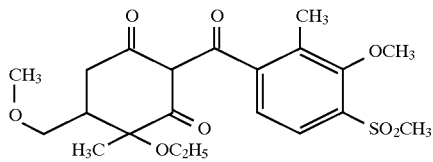

4-ethoxy-5-methoxymethyl-4-methylcyclohexane-1,3-dione in an amount of 3.55 g (16.6 mmol) was dissolved in methylene chloride in a volume of 25 ml, and the solution was allowed to stirring for 5 minutes under cooling with ice following to an addition of triethylamine in an amount of 2.1 g (20.8 mmol). The solution was then further slowly fed dropwise with 25 ml methylene chloride solution of 3-methoxy-2-methyl-4-methylsulfonylbenzoyl chloride in an amount of 4.34 g (16.6 mmol). After stirring the mixture for 1 hour at an ambient temperature, the mixture was then added with both water and diluted hydrochloric acid to extract it, and the organic solvent layer resulted was then washed with an aqueous solution of sodium hydrogencarbonate and subsequently with saturated saline solution, dried with magnesium sulfate, and the solvent remained was removed by distillation. A crude product obtained was dissolved in acetonitrile in a volume of 50 ml, and the solution was then allowed to a reaction for 15 hours at an ambient temperature following to an addition of both triethylamine in an amount of 2.1 g (20.8 mmol) and acetone cyanohydrin in an amount of 0.14 g (1.65 mmol). The solvent used was removed by distillation under reduced pressure, and the residue was dissolved in methylene chloride. The solution was then washed with diluted hydrochloric acid and saturated saline solution in series and dried with magnesium sulfate, and the solvent remained was removed by distillation, affording a substance in an amount of 7.45 g in an amorphous state. The yield was 97%.

(3) Manufacturing of 4-ethoxy-5-hydroxymethyl-2-(3-methoxy-2-methyl-4-methylsulfonylbenzoyl)-4-methylcyclohexane-1,3-dione.

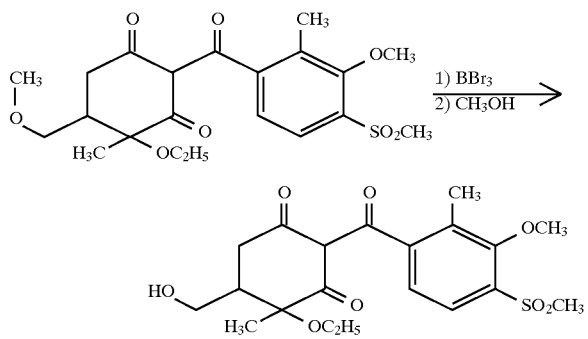

4-ethoxy-5-methoxymethyl-2-(3-methoxy-2-methyl-4-methylsulfonybenzoyl)-4-methylcyclohexane-1,3-dione in an amount of 2.9 g (6.6 mmol) was dissolved in methylene chloride in a volume of 20 ml, and the solution was then fed dropwise with 10 ml methylene chloride solution of boron tribromide in an amount of 1.65 g (6.6 mmol) at 0° C. and was subsequently allowed to stirring for 1 hour at 0° C. Methanol and water both in a small amount were added to the reacted-solution to extract it, and the organic solvent layer resulted was washed with saturated saline solution and dried with magnesium sulfate, and the solvent remained was removed by distillation to obtain a crude product.

The crude product obtained was then purified by means of silica gel column chromatography, where a mixture of chloroform and methanol at a combining ratio of 30 to 1 is used, affording an objective compound in an amount of 1.0 g in an amorphous state. The yield was 36%.

(4) Manufacturing of 5-ethoxy-3-(3-methoxy-2-methyl-4-methylsulfonylbenzoyl)-5-methylbicyclo[4,1,0]heptane-2,4-dione (cis-form).

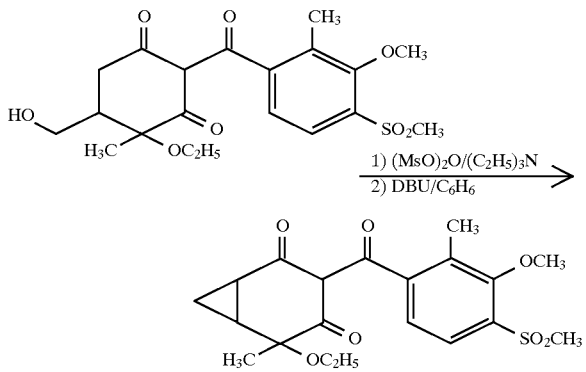

4-ethoxy-5-hydroxymethyl-2-(3-methoxy-2-methyl-4-methylsullfonylbenzoyl)-4-methylcyclohexane-1,3-dione in an amount of 1.0 g (2.35 mmol) was dissolved in methylene chloride in a volume of 10 ml, and the solution was stirred for 1 hour at 0° C. following to an addition of both triethylamine in an amount of 0.26 g (2.57 mmol) and methanesulfonic acid an hydride in an amount of 0.45 g (2.57 mmol) thereto. The reacted-solution was then added with both water and diluted hydrochloric acid to adjust it to acidic condition for a subsequent extraction with methylene chloride. The organic solvent layer resulted was washed with saturated saline solution and dried with magnesium sulfate, and the solvent remained was removed by distillation, thereby affording a crude product. The obtained crude product in an amount of 0.5 g (0.99 mmol) was then dissolved in benzene in a volume of 5 ml, and the solution was stirred for 2 hours at 60° C. following to an addition of 1,8-diaza-bicyclo[5,4,0]unde-7-cene in a volume of 0.3 ml (1.94 mml). After removing the solvent by distillation under reduced pressure, the reacted-solution was added with both water and diluted hydrochloric acid to adjust it to acidic condition and then extracted with methylene chloride. The organic solvent layer resulted was washed with saturated saline solution and dried with magnesium sulfate, and the solvent remained was removed by distillation. A crude product obtained was then separated by means of thin layer chromatography using silica gel, where a mixture of chloroform and methanol at a combining ration of 20 to 1 is used, to obtain the objective compound in an amount of 0.35 g in an amorphous state. The yield was 86%.

(EXAMPLE 2)

Manufacturing of 3-(3-methoxy-2-methyl-4-methylsulfonylbenzoyl)-5-methyl-(2-propyloxy)bicyclo[4,1,0]heptane-2,4-dione (cis and trans forms).

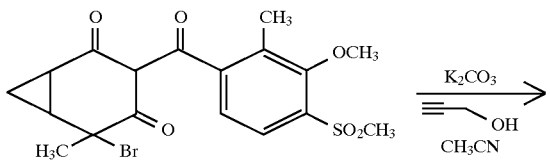

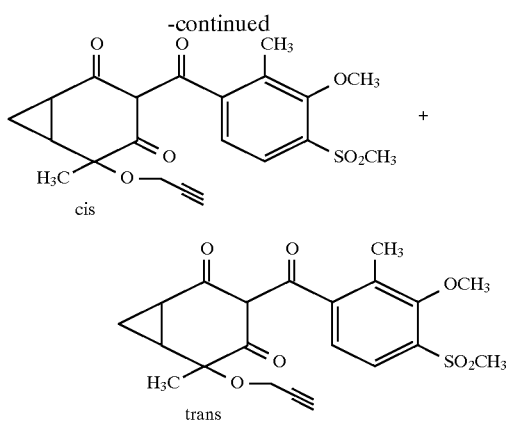

5-bromo-3-(3-methoxy-2-methyl-4-methylsulfonylbenzoyl)-5-methylbicyclo[4,1,0]heptane-2,4-dione in an amount of 0.88 g (2.0 mmol) was dissolved in a mixture of acetonitrile in a volume of 5 ml and propargyl alcohol in a volume of 5 ml, and the solution was then stirred for 15 hours at an ambient temperature following to an addition of potassium carbonate in an amount of 0.28 g (2.0 mmol). After removing the solvents by distillation under reduced pressure, the solution was then added with both water and diluted hydrochloric acid to adjust it to an acidic condition and was subsequently extracted with methylene chloride. The organic solvent layer resulted was then washed with saturated saline solution and dried with magnesium sulfate, and the solvent remained was removed by distillation. A crude product obtained was then separated by means of thin layer chromatography using silica gel, where a mixture of chloroform and methanol at a combining ratio of 30 to 1 is used, affording a trans-form of the objective compound in an amount of 0.26 g and the cis-form in an amount of 0.19 g both in an amorphous state. The yield for the trans-form was 31%, whereas that of the cis-form was 23%.

(Referential Example 1)

Manufacturing of 5-bromo-3-(3-methoxy-2-methyl-4-methylsulforylbenzoyl)-5-methylbicyclo[4,1,0]heptane-2,4-dione.

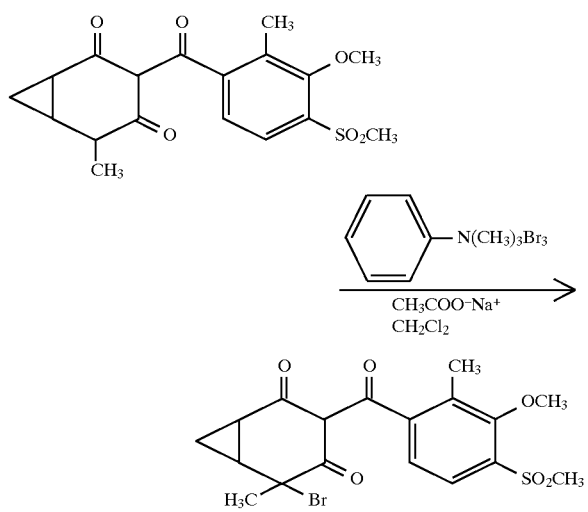

3-(3-methoxy-2-methyl-4-methytsulfonylbenzoyl)-5-methylbicyclo[4,1,0]heptane-2,4-dione in an amount of 5.00 g was dissolved in methylene chloride in a volume of 50 ml, and the solution was then stirred for 70 hours at an ambient temperature following to an addition of both sodium acetate in an amount of 1.35 g and phenyltrimethyl ammonium bromide (herein after abbreviated as PTAB) in an amount of 5.16 g. After the reaction, the reacted-solution was added with water to extract it with methylene chloride. The organic solvent layer resulted was washed with saturated saline solution and dried with magnesium sulfate, and the solvent remained was removed by distillation. The residue obtained was purified by means of silica gel column chromatography to obtain the objective compound in an amount of 1.67 g in pale-yellowish crystalline state. The melting of the compound was in a range of from 155° to 158° C.

(EXAMPLE 3)

Manufacturing of 5-methoxy-3-(3-methoxy-2-methyl-4-methylsulfonyibenzoyl)-5-methylbicyclo[4,1,0]heptane-2,4-dione (cis and trans forms).

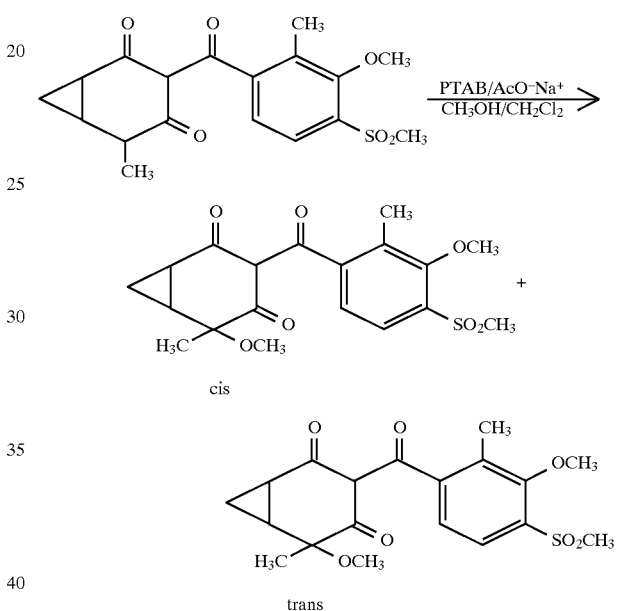

3-(3-methoxy-2-methyl-4-methylsulfonylbenzoyl)-5-methylbicyclo[4,1,0]heptane-2,4-dione in an amount of 6.0 g was dissolved in a mixture consisting of methanol in a volume of 20 ml and methylene chloride in a volume of 40 ml, and the solution was then added with sodium acetate in an amount of 3.38 g and subsequently with phenyltrimethyl ammonium trobromide (PTAB) in an amount of 9.31 g. The mixture was then allowed to a reaction for 3 hours under reflux. After adding sodium acetate in an amount of 1.35 g to the reacted-mixture, the mixture was further allowed to a reaction for 15 hours at an ambient temperature. The reacted-mixture was then condensed under reduced pressure, and the residue obtained was dissolved in a mixture of water and methylene chloride, then adjusted to an acidic condition with diluted hydrochloric acid for the subsequent extraction. The organic solvent layer resulted was washed with saturated saline solution and dried with magnesium sulfate, and the solvent remained was removed by distillation, thereby affording an oily product in an amount of 8.60 g in viscous liquid state. The crude oily product was then purified by means of column chromatography to obtain a trans-form of the objective compound in an amount of 2.35 g and the cis-form in an amount of 1.13 g. The melting points of the trans-form and the cis-form were 190°–193° C. and 169°–170° C., respectively.

(EXAMPLE 4)

Manufacturing of 5-methoxy-3-(4-methylsulfonyl-2-nitrobenzoyl)-5-methylbicyclo[4,1,0]heptane-2,4-dione (cis and trans forms).

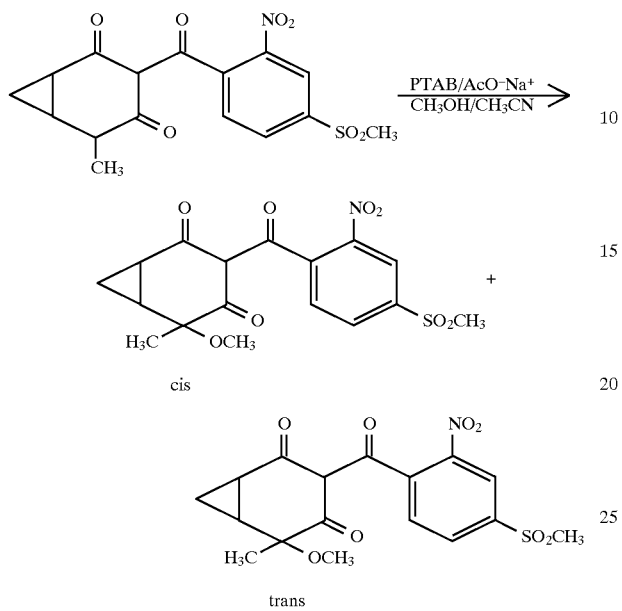

3-(4-methylsulfonyl-2-nitrobenzoyl)-5-methylbicyclo[4,1,0]heptane-2,4-dione in an amount of 3.48 g (10.0 mmol) was dissolved in a mixture of acetonitrile in a volume of 10 ml and methanol in a volume of 10 ml, and the solution was then stirred for 15 hours at an ambient temperature following to an addition of both PTAB in an amount of 4.5 g (12.0 mmol) and sodium acetate in an amount of 1.7 g (20.7 mmol). After removing the solvents by distillation under reduced pressure, the solution was then added with both water and diluted hydrochloric acid to adjust it to an acidic condition and was subsequently extracted with methylene chloride. The organic solvent layer resulted was then washed with saturated saline solution and dried with magnesium sulfate, and the solvent remained was removed by distillation. A crude product obtained was then separated by means of thin layer chromatography using silica gel, where a mixture of chloroform and methanol at a combining ratio of 30 to 1 is used, affording a trans-form of the objective compound in an amount of 0.9 g and the cis-form in an amount of 0.45 g both in an amorphous state. The yield for the trans-form was 24% whereas that of the cis-form was 12%.

(EXAMPLE 5)

Manufacturing of 3-(3-difluoromethoxy-2-methyl-4-methylsulfonylbenzoyl)-5-methoxy-5-methylbicyclo[4,1,0]heptane-2,4-dione (cis and trans forms).

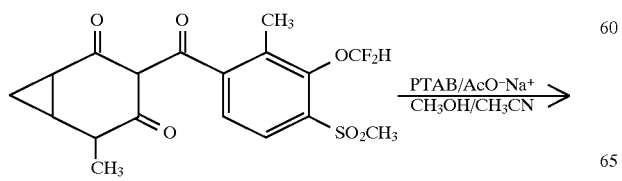

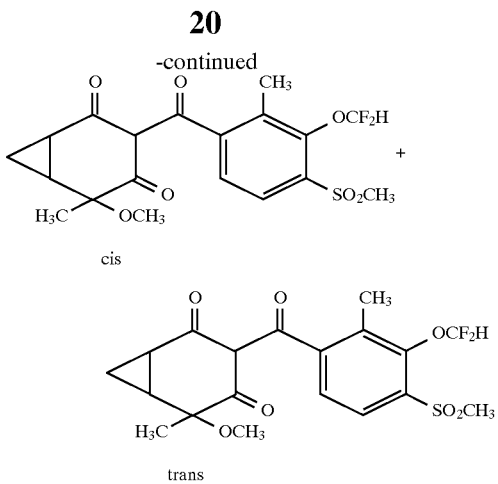

3-(3-difluoromethoxy-2-methyl-4-methylsulfonylbenzoyl)-5-methylbicyclo[4,1,0]heptane-2,4-dione in an amount of 0.70 g (1.75 mmol) was dissolved in a mixture of acetonitrile in a volume of 5 ml and methanol in a volume of 5 ml, and the solution was then stirred for 15 hours at an ambient temperature following to an addition of both PTAB in an amount of 0.8 g (2.13 mmol) and sodium acetate in an amount of 0.3 g (3.66 mmol). After removing the solvents by distillation under reduced pressure, the solution was added with both water and diluted hydrochloric acid to adjust it to an acidic condition and was subsequently extracted with methylene chloride. The organic solvent layer resulted was then washed with saturated saline solution and dried with magnesium sulfate, and the solvent remained was removed by distillation. A crude product obtained was then separated by means of thin layer chromatography using silica gel, where a mixture of chloroform and methanol at a combining ratio of 30 to 1 is used, affording a trans-form of the objective compound in an amount of 0.24 g and the cis-form in an amount of 0.20 g both in an amorphous state. The yield for the trans-form was 32% whereas that of the cis-form was 27%.

(Referential Example 2)

Manufacturing of 3-(3-difluoromethoxy-2-methyl-4-methylsultonylbenzoyl)-5-methylbicyclo[4,1,0]heptane-2,4-dione (cis-form).

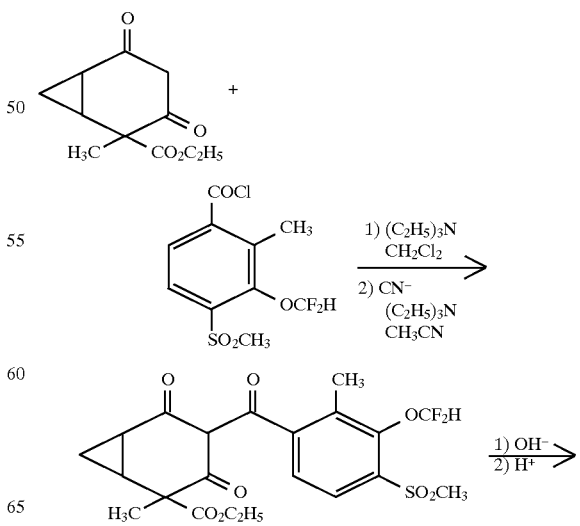

-continued

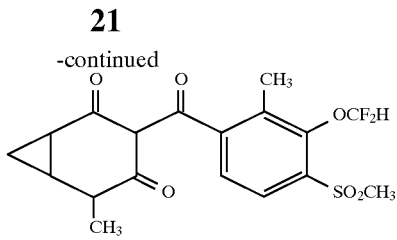

To methylene chloride in a volume of 30 ml, were dissolved 5-ethoxycarbonyl-5-methylbicyclo[4,1,0]heptane-2,4-dione (trans-form) in an amount of 3.15 g and 3-difluoromethoxy-2-methyl-4-methylsulfonylbenzoly chloride in an amount of 4.56 g, and the solution was then fed dropwise with triethylamine in an amount of 1.67 g while stirring under cooling by using ice water. After cooling to an ambient temperature, the mixture was further stirred for 1 hour, and the reaction mixture was then washed with each of diluted hydrochloric acid, an aqueous solution of sodium hydrogencarbonate and saturated saline solution in series. Then, the organic layer was dried with magnesium sulfate, and the solvent was removed by distillation under reduced pressure, thereby affording an oily product. The product was then dissolved in acetonitrile in a volume of 30 ml and subsequently added with both triethylamine in an amount of 1.82 g and acetone cyanohydrin in an amount of 0.06 g, then the mixture was allowed to a reaction for 40 hours. After the reaction, the reaction mixture was added with diluted hydrochloric acid to extract it with methylene chloride. Then, the organic was washed with each of an aqueous solution of sodium hydrogencarbonate, water and saturated saline solution in series and dried with magnesium sulfate, and the solvent was removed by distillation under reduced pressure. The residue obtained was purified by means of silicagel column chromatography using chloroform, affording powder product in an amount of 5.03 g.
$^1$H-NMR (d, CDC$_3$):0.73 (q, J=5, 5Hz, 1H), 1.27 (t, J=7.2 Hz, 3H), 1.46 (s, 3H), 1.66 (m, 1H), 2.28 (s, 3H), 2.3 (m, 1H), 3.23 (s, 3H), 4.18 (q, J=7.2, 2H), 6.72 (t, J=75.0, 1H), 7.11 (d, J=8.1, 1H) 7.88 (d, J=8.1, 1H), 17.42 (bs, 1H)

3-(3-difluoromethoxy-2-methyl-4-methylsulfonylberzoyl)-5-ethoxycarbonyl-5-methylbicyclo[4,1,0]heptane-2,4-dione in the trans-form in an amount of 1.84 g was dissolved in methylene chloride in a volume of 20 ml, and the solution was allowed to a reaction for 1 hour at an ambient temperature under reflux following to an addition of 1-N aqueous solution of sodium hydroxide in a volume of 11.7 ml to the solution. After proceeding hydrolysis in the above reaction, the reacted solution was then fed dropwise with both acetic acid in an amount of 0.70 g and methylene chloride in a volume of 5 ml under cooling with ice water, then neutralized and allowed to a decarboxylation reaction. After 1 hour, the organic layer resulted was separated, washed with water and subsequently with saturated saline solution and dried with magnesium sulfate. After removing the solvent, a crude crystalline product precipitated was further subjected to recrystallization procedure in methanol, thereby affording the objective compound in an amount of 0.67 g in a form of whitish crystals. The melting point of the compound was 152°–156 ° C.
$^1$H-NMR (d, CDCl$_3$, δ ppm):0.77 (m, 1H), 1.20, 1.49 (d, J=6, 6Hz, 3H), 1.9 (m, 3H), 2.23, 2.28 (s, 3H), 2.78 (m, 1H), 3.21 (s, 3H), 6.69 (t, J=75.0, 1H), 7.05 (bd, J=8.4, 1H), 7.88 (d, J=8.4, 1H), 17.5 (bs, 1H)

(Referential Example 3)

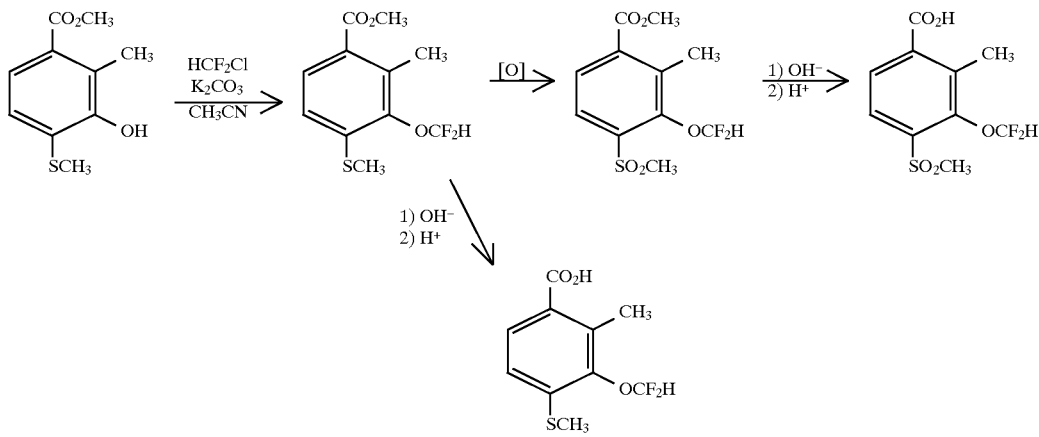

(1) Manufacturing of 3-difluoromethoxy-2-methyl-4-methylthiobenzoic acid

To an autoclave made of metal in a volume of 200 ml, were placed 3-hydroxy-2-methyl-4-methylthiobenzoic acid methyl ester in an amount of 22.2 g, acetonitrile in an amount of 100 ml and potassium carbonate in an amount of 13.7 g, and the mixture was allowed to a reaction for 3.5 hours at 100° C. following to a blowing of chlorodifluoro methane in an amount of 21 g into the autoclave at an ambient temperature. The reacted-solution was then poured into water and then extracted with ethyl acetate. The organic solvent layer resulted was washed with water and subsequently with saturated saline solution and then dried with magnesium sulfate, and the solvent remained was removed by distillation. The residue resulted was then purified by means of silica gel column chromatography, which uses a developer consisting of n-hexane and benzene, affording a methyl ester of the objective compound in an amount of 9.08 g. The methyl ester in an amount of 1.00 g was then dissolved in ethanol in a volume of 10 ml, and the solution was allowed to hydrolysis for 2 hours at a temperature of from 70° to 80° C. following to an addition of 1-N solution of sodium hydroxide in an amount of 7.6 ml. After removing the solvent therein by distillation, the residue was dissolved in water and then adjusted to an acidic condition with diluted hydrochloric acid for a subsequent extraction thereof with ethyl acetate. The organic solvent layer resulted was washed with saturated saline solution, then dried with magnesium sulfate, and the solvent remained was removed by distillation, thereby affording the objective compound in an amount of 0.94 g in white crystalline state. The melting point of the compound was 200°–204° C.

(2) Manufacturing of 3-difluoromethoxy-2-methyl-4-methylsulforylbenzoic acid 3-difluoromethoxy-2-methyl-4-methylthiobenzoic acid methyl ester in an amount of 4.22 g was dissolved in acetic acid in a volume of 20 ml, and the solution was then fed dropwise with 30% aqueous solution of hydrogen peroxide in an amount of 1.60 g at 60° C. After raising the temperature of the mixture to 100° C., 30% aqueous solution of hydrogen peroxide in an amount of 3.21 g was further fed dropwise to the mixture. After dropping, the mixture was allowed to a reaction for 2 hours under reflux, and the mixture was poured into water to extract it with ethyl acetate following to cooling the reacted-mixture. The organic solvent layer resulted was washed with each of hypo and saturated saline solution in series, the solvent remained was removed by distillation, thereby affording a methyl ester of the objective compound. The said methyl ester was then subjected to the same procedure as described above to obtain the objective compound in an amount of 4.28 g in whitish crystalline state. The melting point of the compound was 151°–153 ° C.

The representative examples of the compounds according to the present invention are presented in the Tables from 1 through 4 as presented below, where all compounds prepared in the examples described above are included.

TABLE 1

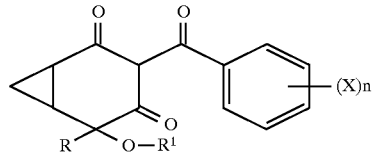

| Compound No. | R | $R^1$ | Configuration | (X)n | Physical Constant [ ]mp °C. |
|---|---|---|---|---|---|
| I-1 | $CH_3$ | $CH_3$ | cis | 2-$NO_2$-4-Cl | powder |
| I-2 | $CH_3$ | $CH_3$ | trans | 2-$NO_2$-4-Cl | powder |
| I-3 | $CH_3$ | $CH_3$ | cis | 2-$NO_2$-4-$CF_3$ | powder |
| I-4 | $CH_3$ | $CH_3$ | trans | 2-$NO_2$-4-$CF_3$ | powder |
| I-5 | $CH_3$ | $CH_3$ | cis | 2-$NO_2$-4-$SCH_3$ | powder |
| I-6 | $CH_3$ | $CH_3$ | trans | 2-$NO_2$-4-$SCH_3$ | powder |
| I-7 | $CH_3$ | $CH_3$ | cis | 2-$NO_2$-4-$SO_2CH_3$ | powder |
| I-8 | $CH_3$ | $CH_3$ | trans | 2-$NO_2$-4-$SO_2CH_3$ | powder |
| I-9 | $CH_3$ | $CH_3$ | cis | 2-Cl-4-$SO_2CH_3$ | powder |
| I-10 | $CH_3$ | $CH_3$ | trans | 2-Cl-4-$SO_2CH_3$ | powder |
| I-11 | $CH_3$ | $CH_3$ | cis | 2,3,4-$Cl_3$ | powder |
| I-12 | $CH_3$ | $CH_3$ | trans | 2,3,4-$Cl_3$ | 125–127 |
| I-13 | $CH_3$ | $CH_3$ | cis | 2,3-$Cl_2$-4-$SO_2CH_3$ | powder |
| I-14 | $CH_3$ | $CH_3$ | trans | 2,3-$Cl_2$-4-$SO_2CH_3$ | powder |
| I-15 | $CH_3$ | $CH_3$ | cis | 2,3-$(CH_3)_2$-4-$SO_2CH_3$ | powder |
| I-16 | $CH_3$ | $CH_3$ | trans | 2,3-$(CH_3)_2$-4-$SO_2CH_3$ | powder |
| I-17 | $CH_3$ | $CH_3$ | cis | 2-Cl-3-$OCH_3$-4-$SO_2CH_3$ | powder |
| I-18 | $CH_3$ | $CH_3$ | trans | 2-Cl-3-$OCH_3$-4-$SO_2CH_3$ | 168–170 |
| I-19 | $CH_3$ | $C_2H_5$ | cis | 2-Cl-3-$OCH_3$-4-$SO_2CH_3$ | powder |
| I-20 | $CH_3$ | $C_2H_5$ | trans | 2-Cl-3-$OCH_3$-4-$SO_2CH_3$ | powder |
| I-21 | $CH_3$ | $CH_2CF_3$ | cis | 2-Cl-3-$OCH_3$-4-$SO_2CH_3$ |  |
| I-22 | $CH_3$ | $CH_2CF_3$ | trans | 2-Cl-3-$OCH_3$-4-$SO_2CH_3$ | powder |
| I-23 | $CH_3$ | $iC_3H_7$ | cis | 2-Cl-3-$OCH_3$-4-$SO_2CH_3$ |  |
| I-24 | $CH_3$ | $iC_3H_7$ | trans | 2-Cl-3-$OCH_3$-4-$SO_2CH_3$ | powder |
| I-25 | $CH_3$ | H | cis | 2-$CH_3$-3-$OCH_3$-4-$SO_2CH_3$ | 170–174 |
| I-26 | $CH_3$ | H | trans | 2-$CH_3$-3-$OCH_3$-4-$SO_2CH_3$ | powder |
| I-27 | $CH_3$ | $CH_3$ | cis | 2-$CH_3$-3-$OCH_3$-4-$SO_2CH_3$ | 169–170 |
| I-28 | $CH_3$ | $CH_3$ | trans | 2-$CH_3$-3-$OCH_3$-4-$SO_2CH_3$ | 190–193 |
| I-29 | $CH_3$ | $C_2H_5$ | cis | 2-$CH_3$-3-$OCH_3$-4-$SO_2CH_3$ | powder |
| I-30 | $CH_3$ | $C_2H_5$ | trans | 2-$CH_3$-3-$OCH_3$-4-$SO_2CH_3$ | 174–176 |
| I-31 | $CH_3$ | $nC_3H_7$ | cis | 2-$CH_3$-3-$OCH_3$-4-$SO_2CH_3$ | powder |
| I-32 | $CH_3$ | $nC_3H_7$ | trans | 2-$CH_3$-3-$OCH_3$-4-$SO_2CH_3$ | powder |
| I-33 | $CH_3$ | $iC_3H_7$ | cis | 2-$CH_3$-3-$OCH_3$-4-$SO_2CH_3$ | powder |
| I-34 | $CH_3$ | $iC_3H_7$ | trans | 2-$CH_3$-3-$OCH_3$-4-$SO_2CH_3$ | powder |
| I-35 | $CH_3$ | $CH_2CH=CH_2$ | cis | 2-$CH_3$-3-$OCH_3$-4-$SO_2CH_3$ | powder |
| I-36 | $CH_3$ | $CH_2CH=CH_2$ | trans | 2-$CH_3$-3-$OCH_3$-4-$SO_2CH_3$ | powder |
| I-37 | $CH_3$ | $CH_2C\equiv CH$ | cis | 2-$CH_3$-3-$OCH_3$-4-$SO_2CH_3$ | powder |
| I-38 | $CH_3$ | $CH_2C\equiv CH$ | trans | 2-$CH_3$-3-$OCH_3$-4-$SO_2CH_3$ | powder |
| I-39 | $CH_3$ | $C_2H_4OCH_3$ | cis | 2-$CH_3$-3-$OCH_3$-4-$SO_2CH_3$ | powder |
| I-40 | $CH_3$ | $C_2H_4OCH_3$ | trans | 2-$CH_3$-3-$OCH_3$-4-$SO_2CH_3$ | powder |
| I-41 | $CH_3$ | $CH_3$ | cis | 2-$CH_3$-3-$OCHF_2$-4-$SO_2CH_3$ | powder |
| I-42 | $CH_3$ | $CH_3$ | trans | 2-$CH_3$-3-$OCHF_2$-4-$SO_2CH_3$ | viscous oil |
| I-43 | $CH_3$ | $^nBu$ | cis | 2-$CH_3$-3-$OCH_3$-4-$SO_2CH_3$ | powder |
| I-44 | $CH_3$ | $^nBu$ | trans | 2-$CH_3$-3-$OCH_3$-4-$SO_2CH_3$ | powder |
| I-45 | $CH_3$ | $^iBu$ | cis | 2-$CH_3$-3-$OCH_3$-4-$SO_2CH_3$ | powder |
| I-46 | $CH_3$ | $^iBu$ | trans | 2-$CH_3$-3-$OCH_3$-4-$SO_2CH_3$ | powder |

TABLE 1-continued

| Compound No. | R | $R^1$ | Configuration | (X)n | Physical Constant [ ]mp °C. |
|---|---|---|---|---|---|
| I-47 | $CH_3$ | $CH_2$-cPr | cis | 2-$CH_3$-3-$OCH_3$-4-$SO_2CH_3$ | powder |
| I-48 | $CH_3$ | $CH_2$-cPr | trans | 2-CHa-3-$OCH_3$-4-$SO_2CH_3$ | powder |
| I-49 | $CH_3$ | $CH_2Ph$ | | 2-$CH_3$-3-$OCH_3$-4-$SO_2CH_3$ | powder |
| I-50 | $CH_3$ | $cC_5H_9$ | cis | 2-$CH_3$-3-$OCH_3$-4-$SO_2CH_3$ | powder |
| I-51 | $CH_3$ | $cC_5H_9$ | trans | 2-$CH_3$-3-$OCH_3$-4-$SO_2CH_3$ | powder |
| I-52 | $CH_3$ | $CH_2COCH_3$ | cis | 2-$CH_3$-3-$OCH_3$-4-$SO_2CH_3$ | powder |
| I-53 | $CH_3$ | $CH_2COCH_3$ | trans | 2-$CH_3$-3-$OCH_3$-4-$SO_2CH_3$ | powder |
| I-54 | $CH_3$ | $CH_2CH_2Cl$ | cis | 2-$CH_3$-3-$OCH_3$-4-$SO_2CH_3$ | powder |
| I-55 | $CH_3$ | $CH_2CH_2Cl$ | trans | 2-$CH_3$-3-$OCH_3$-4-$SO_2CH_3$ | powder |
| I-56 | $CH_3$ | $CH_2CH_2Br$ | cis | 2-$CH_3$-3-$OCH_3$-4-$SO_2CH_3$ | powder |
| I-57 | $CH_3$ | $CH_2CH_2Br$ | trans | 2-$CH_3$-3-$OCH_3$-4-$SO_2CH_3$ | powder |
| I-58 | $CH_3$ | $CH_2CH_2CN$ | cis | 2-$CH_3$-3-$OCH_3$-4-$SO_2CH_3$ | powder |
| I-59 | $CH_3$ | $CH_2CH_2CN$ | trans | 2-$CH_3$-3-$OCH_3$-4-$SO_2CH_3$ | powder |
| I-60 | $CH_3$ | $CH_2CH_2OH$ | cis | 2-$CH_3$-3-$OCH_3$-4-$SO_2CH_3$ | powder |
| I-61 | $CH_3$ | $CH_2CH_2OH$ | trans | 2-$CH_3$-3-$OCH_3$-4-$SO_2CH_3$ | |
| I-62 | $CH_3$ | C(O)H | cis | 2-$CH_3$-3-$OCH_3$-4-$SO_2CH_3$ | powder |
| I-63 | $CH_3$ | C(O)H | trans | 2-$CH_3$-3-$OCH_3$-4-$SO_2CH_3$ | |
| I-64 | $CH_3$ | $COCH_3$ | cis | 2-$CH_3$-3-$OCH_3$-4-$SO_2CH_3$ | powder |
| I-65 | $CH_3$ | $COCH_3$ | trans | 2-$CH_3$-3-$OCH_3$-4-$SO_2CH_3$ | powder |
| I-66 | $CH_3$ | $COC_2H_5$ | cis | 2-$CH_3$-3-$OCH_3$-4-$SO_2CH_3$ | powder |
| I-67 | $CH_3$ | $COC_2H_5$ | trans | 2-$CH_3$-3-$OCH_3$-4-$SO_2CH_3$ | powder |
| I-68 | $CH_3$ | COPh | cis | 2-$CH_3$-3-$OCH_3$-4-$SO_2CH_3$ | powder |
| I-69 | $CH_3$ | COPh | trans | 2-$CH_3$-3-$OCH_3$-4-$SO_2CH_3$ | powder |
| I-70 | $CH_3$ | $CH_3$ | cis | 2-$CH_3$-4-$SO_2CH_3$ | powder |
| I-71 | $CH_3$ | $CH_3$ | trans | 2-$CH_3$-4-$SO_2CH_3$ | powder |
| I-72 | $CH_3$ | $CH_3$ | cis | 2-$OCH_3$-4-$SO_2CH_3$ | powder |
| I-73 | $CH_3$ | $CH_3$ | trans | 2-$OCH_3$-4-$SO_2CH_3$ | powder |
| I-74 | $CH_3$ | $CH_3$ | cis | 2-$SO_2CH_3$-4-Cl | powder |
| I-75 | $CH_3$ | $CH_3$ | trans | 2-$SO_2CH_3$-4-Cl | powder |
| I-76 | $CH_3$ | $CH_3$ | cis | 2-$CH_3$-3-Br-4-$SO_2CH_3$ | 176–177 |
| I-77 | $CH_3$ | $CH_3$ | trans | 2-$CH_3$-3-Br-4-$SO_2CH_3$ | 182 dec. |
| I-78 | $CH_3$ | $CH_3$ | cis | 2,3-$(OCH_3)_2$-4-$SO_2CH_3$ | 183–186 |
| I-79 | $CH_3$ | $CH_3$ | trans | 2,3-$(OCH_3)_2$-4-$SO_2CH_3$ | powder |
| I-80 | $CH_3$ | H | cis | 2-Cl-3-$OCH_3$-4-$SO_2CH_3$ | powder |
| I-81 | $CH_3$ | H | trans | 2-Cl-3-$OCH_3$-4-$SO_2CH_3$ | powder |
| I-82 | $CH_3$ | $^n$Pr | cis | 2-Ci-3-$OCH_3$-4-$SO_2CH_3$ | powder |
| I-83 | $CH_3$ | $^n$Pr | trans | 2-Cl-3-$OCH_3$-4-$SO_2CH_3$ | powder |
| I-84 | $CH_3$ | $^n$Oct | cis | 2-Cl-3-$OCH_3$-4-$SO_2CH_3$ | powder |
| I-85 | $CH_3$ | $^n$Oct | trans | 2-Cl-3-$OCH_3$-4-$SO_2CH_3$ | powder |
| I-86 | $CH_3$ | C(O)H | cis | 2-Cl-3-$OCH_3$-4-$SO_2CH_3$ | powder |
| I-87 | $CH_3$ | C(O)H | trans | 2-Cl-3-$OCH_3$-4-$SO_2CH_3$ | powder |
| I-88 | $CH_3$ | $COCH_3$ | cis | 2-Cl-3-$OCH_3$-4-$SO_2CH_3$ | powder |
| I-89 | $CH_3$ | $COCH_3$ | trans | 2-Cl-3-$OCH_3$-4-$SO_2CH_3$ | powder |
| I-90 | $CH_3$ | $CH_3$ | cis | 2-$CH_3$-3-$OCH_3$-4-$SO_2CH_3$ | Na salt 227–233 dec. |

TABLE 2

| Compound No. | R | $R^1$ | Configuration | (X)n | Physical Constant [ ]mp °C. |
|---|---|---|---|---|---|
| II-1 | $C_2H_5$ | $CH_3$ | cis | 2-$NO_2$-4-Cl | |
| II-2 | $C_2H_5$ | $CH_3$ | trans | 2-$NO_2$-4-Cl | |
| II-3 | $C_2H_5$ | $CH_3$ | cis | 2-$NO_2$-4-$CF_3$ | |
| II-4 | $C_2H_5$ | $CH_3$ | trans | 2-$NO_2$-4-$CF_3$ | |

TABLE 2-continued

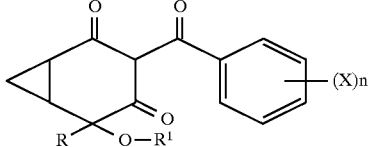

| Compound No. | R | R¹ | Configuration | (X)n | Physical Constant [ ]mp °C. |
|---|---|---|---|---|---|
| II-5 | $C_2H_5$ | $CH_3$ | cis | 2-$NO_2$-4-$SCH_3$ | |
| II-6 | $C_2H_5$ | $CH_3$ | trans | 2-$NO_2$-4-$SCH_3$ | |
| II-7 | $C_2H_5$ | $CH_3$ | cis | 2-$NO_2$-4-$SO_2CH_3$ | |
| II-8 | $C_2H_5$ | $CH_3$ | trans | 2-$NO_2$-4-$SO_2CH_3$ | |
| II-9 | $C_2H_5$ | $CH_3$ | cis | 2-Cl-4-$SO_2CH_3$ | |
| II-10 | $C_2H_5$ | $CH_3$ | trans | 2-Cl-4-$SO_2CH_3$ | |
| II-11 | $C_2H_5$ | $CH_3$ | cis | 2,3,4-$Cl_3$ | |
| II-12 | $C_2H_5$ | $CH_3$ | trans | 2,3,4-$Cl_3$ | |
| II-13 | $C_2H_5$ | $CH_3$ | cis | 2,3-$Cl_2$-4-$SO_2CH_3$ | |
| II-14 | $C_2H_5$ | $CH_3$ | trans | 2,3-$Cl_2$-4-$SO_2CH_3$ | |
| II-15 | $C_2H_5$ | $CH_3$ | cis | 2,3-$(CH_3)_2$-4-$SO_2CH_3$ | |
| II-16 | $C_2H_5$ | $CH_3$ | trans | 2,3-$(CH_3)_2$-4-$SO_2CH_3$ | |
| II-17 | $C_2H_5$ | $CH_3$ | cis | 2-Cl-3-$OCH_3$-4-$SO_2CH_3$ | |
| II-18 | $C_2H_5$ | $CH_3$ | trans | 2-Cl-3-$OCH_3$-4-$SO_2CH_3$ | |
| II-19 | $C_2H_5$ | $C_2H_5$ | cis | 2-Cl-3-$OCH_3$-4-$SO_2CH_3$ | |
| II-20 | $C_2H_5$ | $C_2H_5$ | trans | 2-Cl-3-$OCH_3$-4-$SO_2CH_3$ | |
| II-21 | $C_2H_5$ | $CH_2CF_3$ | cis | 2-Cl-3-$OCH_3$-4-$SO_2CH_3$ | |
| II-22 | $C_2H_5$ | $CH_2CF_3$ | trans | 2-Cl-3-$OCH_3$-4-$SO_2CH_3$ | |
| II-23 | $C_2H_5$ | $iC_3H_7$ | cis | 2-Cl-3-$OCH_3$-4-$SO_2CH_3$ | |
| II-24 | $C_2H_5$ | $iC_3H_7$ | trans | 2-Cl-3-$OCH_3$-4-$SO_2CH_3$ | |
| II-25 | $C_2H_5$ | H | cis | 2-$CH_3$-3-$OCH_3$-4-$SO_2CH_3$ | |
| II-26 | $C_2H_5$ | H | trans | 2-$CH_3$-3-$OCH_3$-4-$SO_2CH_3$ | |
| II-27 | $C_2H_5$ | $CH_3$ | cis | 2-$CH_3$-3-$OCH_3$-4-$SO_2CH_3$ | powder |
| II-28 | $C_2H_5$ | $CH_3$ | trans | 2-$CH_3$-3-$OCH_3$-4-$SO_2CH_3$ | |
| II-29 | $C_2H_5$ | $C_2H_5$ | cis | 2-$CH_3$-3-$OCH_3$-4-$SO_2CH_3$ | |
| II-30 | $C_2H_5$ | $C_2H_5$ | trans | 2-$CH_3$-3-$OCH_3$-4-$SO_2CH_3$ | |
| II-31 | $C_2H_5$ | $nC_3H_7$ | cis | 2-$CH_3$-3-$OCH_3$-4-$SO_2CH_3$ | powder |
| II-32 | $C_2H_5$ | $nC_3H_7$ | trans | 2-$CH_3$-3-$OCH_3$-4-$SO_2CH_3$ | powder |
| II-33 | $C_2H_5$ | $iC_3H_7$ | cis | 2-$CH_3$-3-$OCH_3$-4-$SO_2CH_3$ | |
| II-34 | $C_2H_5$ | $iC_3H_7$ | trans | 2-$CH_3$-3-$OCH_3$-4-$SO_2CH_3$ | |
| II-35 | $C_2H_5$ | $CH_2CH=CH_2$ | cis | 2-$CH_3$-3-$OCH_3$-4-$SO_2CH_3$ | |
| II-36 | $C_2H_5$ | $CH_2CH=CH_2$ | trans | 2-$CH_3$-3-$OCH_3$-4-$SO_2CH_3$ | |
| II-37 | $C_2H_5$ | $CH_2\equiv CH$ | cis | 2-$CH_3$-3-$OCH_3$-4-$SO_2CH_3$ | |
| II-38 | $C_2H_5$ | $CH_2\equiv CH$ | trans | 2-$CH_3$-3-$OCH_3$-4-$SO_2CH_3$ | |
| II-39 | $C_2H_5$ | $C_2H_4OCH_3$ | cis | 2-$CH_3$-3-$OCH_3$-4-$SO_2CH_3$ | |
| II-40 | $C_2H_5$ | $C_2H_4OCH_3$ | trans | 2-$CH_3$-3-$OCH_3$-4-$SO_2CH_3$ | |
| II-41 | $C_2H_5$ | $CH_3$ | cis | 2-$CH_3$-3-$OCHF_2$-4-$SO_2CH_3$ | |
| II-42 | $C_2H_5$ | $CH_3$ | trans | 2-$CH_3$-3-$OCHF_2$-4-$SO_2CH_3$ | |

TABLE 3

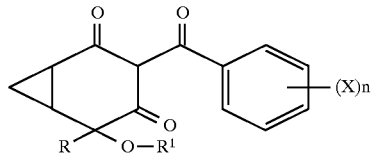

| Compound No. | R | R¹ | Configuration | (X)n | Physical Constant [ ]mp °C. |
|---|---|---|---|---|---|
| III-1 | $iC_3H_7$ | $CH_3$ | cis | 2-$NO_2$-4-Cl | |
| III-2 | $iC_3H_7$ | $CH_3$ | trans | 2-$NO_2$-4-Cl | |
| III-3 | $iC_3H_7$ | $CH_3$ | cis | 2-$NO_2$-4-$CF_3$ | |
| III-4 | $iC_3H_7$ | $CH_3$ | trans | 2-$NO_2$-4-$CF_3$ | |
| III-5 | $iC_3H_7$ | $CH_3$ | cis | 2-$NO_2$-4-$SCH_3$ | |
| III-6 | $iC_3H_7$ | $CH_3$ | trans | 2-$NO_2$-4-$SCH_3$ | |
| III-7 | $iC_3H_7$ | $CH_3$ | cis | 2-$NO_2$-4-$SO_2CH_3$ | |
| III-8 | $iC_3H_7$ | $CH_3$ | trans | 2-$NO_2$-4-$SO_2CH_3$ | |
| III-9 | $iC_3H_7$ | $CH_3$ | cis | 2-Cl-4-$SO_2CH_3$ | |
| III-10 | $iC_3H_7$ | $CH_3$ | trans | 2-Cl-4-$SO_2CH_3$ | |
| III-11 | $iC_3H_7$ | $CH_3$ | cis | 2,3,4-$Cl_3$ | |

TABLE 3-continued

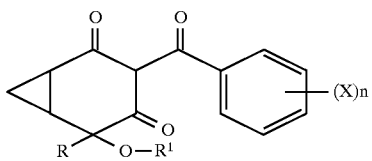

| Compound No. | R | R¹ | Configuration | (X)n | Physical Constant [ ]mp °C. |
|---|---|---|---|---|---|
| III-12 | iC$_3$H$_7$ | CH$_3$ | trans | 2,3,4-Cl$_3$ | |
| III-13 | iC$_3$H$_7$ | CH$_3$ | cis | 2,3-Cl$_2$-4-SO$_2$CH$_3$ | |
| III-14 | iC$_3$H$_7$ | CH$_3$ | trans | 2,3-Cl$_2$-4-SO$_2$CH$_3$ | |
| III-15 | iC$_3$H$_7$ | CH$_3$ | cis | 2,3-(CH$_3$)$_2$-4-SO$_2$CH$_3$ | |
| III-16 | iC$_3$H$_7$ | CH$_3$ | trans | 2,3-(CH$_3$)$_2$-4-SO$_2$CH$_3$ | |
| III-17 | iC$_3$H$_7$ | CH$_3$ | cis | 2-Cl-3-OCH$_3$-4-SO$_2$CH$_3$ | |
| III-18 | iC$_3$H$_7$ | CH$_3$ | trans | 2-Cl-3-OCH$_3$-4-SO$_2$CH$_3$ | |
| III-19 | iC$_3$H$_7$ | C$_2$H$_5$ | cis | 2-Cl-3-OCH$_3$-4-SO$_2$CH$_3$ | |
| III-20 | iC$_3$H$_7$ | C$_2$H$_5$ | trans | 2-Cl-3-OCH$_3$-4-SO$_2$CH$_3$ | |
| III-21 | iC$_3$H$_7$ | CH$_2$CF$_3$ | cis | 2-Cl-3-OCH$_3$-4-SO$_2$CH$_3$ | |
| III-22 | iC$_3$H$_7$ | CH$_2$CF$_3$ | trans | 2-Cl-3-OCH$_3$-4-SO$_2$CH$_3$ | |
| III-23 | iC$_3$H$_7$ | iC$_3$H$_7$ | cis | 2-Cl-3-OCH$_3$-4-SO$_2$CH$_3$ | |
| III-24 | iC$_3$H$_7$ | iC$_3$H$_7$ | trans | 2-Cl-3-OCH$_3$-4-SO$_2$CH$_3$ | |
| III-25 | iC$_3$H$_7$ | H | cis | 2-CH$_3$-3-OCH$_3$-4-SO$_2$CH$_3$ | |
| III-26 | iC$_3$H$_7$ | H | trans | 2-CH$_3$-3-OCH$_3$-4-SO$_2$CH$_3$ | |
| III-27 | iC$_3$H$_7$ | CH$_3$ | cis | 2-CH$_3$-3-OCH$_3$-4-SO$_2$CH$_3$ | |
| III-28 | iC$_3$H$_7$ | CH$_3$ | trans | 2-CH$_3$-3-OCH$_3$-4-SO$_2$CH$_3$ | |
| III-29 | iC$_3$H$_7$ | C$_2$H$_5$ | cis | 2-CH$_3$-3-OCH$_3$-4-SO$_2$CH$_3$ | |
| III-30 | iC$_3$H$_7$ | C$_2$H$_5$ | trans | 2-CH$_3$-3-OCH$_3$-4-SO$_2$CH$_3$ | |
| III-31 | iC$_3$H$_7$ | nC$_3$H$_7$ | cis | 2-CH$_3$-3-OCH$_3$-4-SO$_2$CH$_3$ | |
| III-32 | iC$_3$H$_7$ | nC$_3$H$_7$ | trans | 2-CH$_3$-3-OCH$_3$-4-SO$_2$CH$_3$ | |
| III-33 | iC$_3$H$_7$ | iC$_3$H$_7$ | cis | 2-CH$_3$-3-OCH$_3$-4-SO$_2$CH$_3$ | |
| III-34 | iC$_3$H$_7$ | iC$_3$H$_7$ | trans | 2-CH$_3$-3-OCH$_3$-4-SO$_2$CH$_3$ | |
| III-35 | iC$_3$H$_7$ | CH$_2$CH=CH$_2$ | cis | 2-CH$_3$-3-OCH$_3$-4-SO$_2$CH$_3$ | |
| III-36 | iC$_3$H$_7$ | CH$_2$CH=CH$_2$ | trans | 2-CH$_3$-3-OCH$_3$-4-SO$_2$CH$_3$ | |
| III-37 | iC$_3$H$_7$ | CH$_2$C≡CH | cis | 2-CH$_3$-3-OCH$_3$-4-SO$_2$CH$_3$ | |
| III-38 | iC$_3$H$_7$ | CH$_2$C≡CH | trans | 2-CH$_3$-3-OCH$_3$-4-SO$_2$CH$_3$ | |
| III-39 | iC$_3$H$_7$ | C$_2$H$_4$OCH$_3$ | cis | 2-CH$_3$-3-OCH$_3$-4-SO$_2$CH$_3$ | |
| III-40 | iC$_3$H$_7$ | C$_2$H$_4$OCH$_3$ | trans | 2-CH$_3$-3-OCH$_3$-4-SO$_2$CH$_3$ | |
| III-41 | iC$_3$H$_7$ | CH$_3$ | cis | 2-CH$_3$-3-OCHF$_2$-4-SO$_2$CH$_3$ | |
| III-42 | iC$_3$H$_7$ | CH$_3$ | trans | 2-CH$_3$-3-OCHF$_2$-4-SO$_2$CH$_3$ | |

TABLE 4

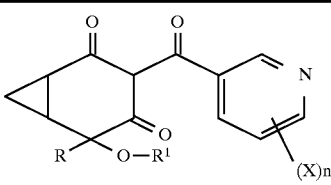

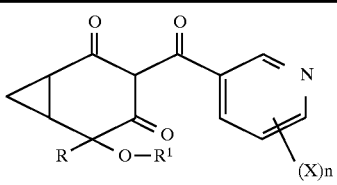

| Compound No. | R | R¹ | Configuration | (X)n | Physical Constant [ ]mp °C. |
|---|---|---|---|---|---|
| IV-1 | CH$_3$ | CH$_3$ | cis | 2-CH$_3$-6-SO$_2$CH$_3$ | powder |
| IV-2 | CH$_3$ | CH$_3$ | trans | 2-CH$_3$-6-SO$_2$CH$_3$ | powder |
| IV-3 | CH$_3$ | C$_2$H$_5$ | cis | 2-CH$_3$-6-SO$_2$CH$_3$ | |
| IV-4 | CH$_3$ | C$_2$H$_5$ | trans | 2-CH$_3$-6-SO$_2$CH$_3$ | |
| IV-5 | CH$_3$ | nC$_3$H$_7$ | cis | 2-CH$_3$-6-SO$_2$CH$_3$ | |
| IV-6 | CH$_3$ | nC$_3$H$_7$ | trans | 2-CH$_3$-6-SO$_2$CH$_3$ | |
| IV-7 | C$_2$H$_5$ | CH$_3$ | cis | 2-CH$_3$-6-SO$_2$CH$_3$ | |
| IV-8 | C$_2$H$_5$ | CH$_3$ | trans | 2-CH$_3$-6-SO$_2$CH$_3$ | |
| IV-9 | C$_2$H$_5$ | C$_2$H$_5$ | cis | 2-CH$_3$-6-SO$_2$CH$_3$ | |
| IV-10 | C$_2$H$_5$ | C$_2$H$_5$ | trans | 2-CH$_3$-6-SO$_2$CH$_3$ | |
| IV-11 | C$_2$H$_5$ | iC$_3$H$_7$ | cis | 2-CH$_3$-6-SO$_2$CH$_3$ | |
| IV-12 | C$_2$H$_5$ | iC$_3$H$_7$ | trans | 2-CH$_3$-6-SO$_2$CH$_3$ | |
| IV-13 | iC$_3$H$_7$ | CH$_3$ | cis | 2-CH$_3$-6-SO$_2$CH$_3$ | |
| IV-14 | iC$_3$H$_7$ | CH$_3$ | trans | 2-CH$_3$-6-SO$_2$CH$_3$ | |
| IV-15 | iC$_3$H$_7$ | C$_2$H$_5$ | cis | 2-CH$_3$-6-SO$_2$CH$_3$ | |
| IV-16 | iC$_3$H$_7$ | C$_2$H$_5$ | trans | 2-CH$_3$-6-SO$_2$CH$_3$ | |
| IV-17 | iC$_3$H$_7$ | nC$_3$H$_7$ | cis | 2-CH$_3$-6-SO$_2$CH$_3$ | |
| IV-18 | iC$_3$H$_7$ | nC$_3$H$_7$ | trans | 2-CH$_3$-6-SO$_2$CH$_3$ | |

$^1$H-NMR Data (CDCl$_3$, δ ppm)

(I-1) 16. 80(bs, 1H, OH)8.17(m, 1H, ArH)7.65(m, 1H, ArH)7.24(m, 1H, ArH) 3.53, 3.30(3H, OCH$_3$)2.17(m, 1H)1.86(m, 2H)1.65, 1.42(3H, CH$_3$)1.10(m, 1H)

(I-2) 16.94, 16.44(1H, OH)8.20(m, 1H, ArH)7.65(m, J=8.1Hz, 1H, ArH) 7.18(d, J=8.1Hz, 1H, ArH)3.32, 3.00 (3H, OCH$_3$)2.17(m, 2H)1.66(m, 1H) 1.63, 1.32(3H, CH$_3$) 0.76(m, 1H)

(I-3) 16.60(bs, 1H, OH)8.45(s, 1H, ArH)7.96(d, J=6.9Hz, 1H, ArH) 7.39(d, J=6.9Hz, 1H, ArH)3.54, 3.30(3H, OCH$_3$ )2.19(m, 1H)1.88(m, 2H) 1.67, 1.43(3H, CH$_3$)1.20 (m, 1H)

(I-4) 16.73, 16.23(1H, OH)8.50(s, 1H, ArH)7.95(d, J=7.6Hz, 1H, ArH) 7.38(d, J=7.6Hz, 1H, ArH)3.34, 3.02 (3H, OCH$_3$)2.16(m, 2H)1.67(m, 1H) 1.69, 1.33(3H, CH$_3$) 0.78(m,1H)

(I-6) 17.20, 16.62(1H, OH)8.00(m, 1H, ArH)7.46(m, 1H, ArH)7.14(m, 1H, ArH) 3.30, 3.00(3H, OCH$_3$)2.58(s, 3H, SCH$_3$)2.24-2.05(m, 2H) 1.70-1.53(m, 4H) 1.30(s, 3H, CH$_3$)0.77(m, 1H)

(I-7) 16.45(bs, 1H, OH)8.74(m, 1H, ArH)8.26(m, 1H, ArH) 7.46(m, 1H, ArH) 3.53, 3.30(3H, OCH$_3$)3.46, 3.16(3H, SO$_2$CH$_3$)2.21(m, 1H)1.92(m, 2H) 1.68, 1.43(3H, CH$_3$) 1.13(m, 1H)

(I-8) 16.58, 16.17(1H, OH)8.76(m, 1H, ArH)8.25(d, J=7.7Hz, 1H, ArH) 7.45(d, J=7.7Hz, 1H, ArH)3.34, 3.16 (3H, OCH$_3$)3.24, 3.02(3H, SO$_2$CH$_3$) 2.20(m, 1H)1.71(m, 2H)1.64, 1.32(3H, CH$_3$)0.78(m, 1H)

(I-9) 17.18, 16.90(1H, OH)7.91(m, 2H, ArH)7.37(m, 1H, ArH)3.53, 3.35(3H, OCH$_3$) 3.14, 3.11 (3H, SO$_2$CH$_3$)2.25 (m, 1H) 1.88(m, 2H) 1.63, 1.54(3H, CH$_3$) 1.15(m, 1H)

(I-10) 17.28, 16.55(1H, OH)7.98(d, J=7.4Hz, 1H, ArH)7.88 (d, J=7.4Hz, 1H, ArH) 7.30(d, J=8.5Hz, 1H, ArH)3.31, 3.13(3H, OCH$_3$)3.10(s, 3H, SO$_2$CH$_3$)2.21(m, 2H) 1.67 (m, 1H)1.66, 1.38(3H, CH$_3$)0.82(m, 1H)

(I-11) 17.22, 16.94(1H, OH)7.45(m, 1H, ArH)7.18-6.95(m, 1H, ArH) 3.52, 3.35(3H, OCH$_3$)2.28-1.70(m, 3H)1.64-1.52(3H, CH$_3$)1.40-1.05(m, 1H)

(I-12) 17.35, 16.55(1H, OH)7.45(m, 1H, ArH)7.20-6.92(m, 1H, ArH) 3.30, 3.12(3H, OCH$_3$)2.30, 2.00(m, 2H)1.72-1.36(m, 4H)0.95-0.72(m, 1H)

(I-13) 17.10, 16.78(1H, OH)8.15(m, 1H, ArH)7.30(m, 1H, ArH)3.50, 3.35(3H, OCH$_3$) 3.28(s, 3H, SO$_2$CH$_3$)2.25(m, 1H)1.90(m, 2H)1.60, 1.50(3H, CH$_3$)1.15(m, 1H)

(I-14) 8.15 (m, 1H, ArH)7.36(m, 1H, ArH)3.32(s, 3H, SO$_2$CH$_3$) 3.32, 3.13(3H, OCH$_3$) 2.21(m, 2H)1.68(m, 1H)1.58, 1.38(3H, CH$_3$)0.82(m, 1H)

(I-15) 17.65, 17.41(1H, OH)7.98(m, 1H, ArH)7.10(m, 1H, ArH)3.55, 3.35(3H, OCH$_3$) 3.10(3H, SO$_2$CH$_3$)2.65(m, 3H, ArCH$_3$)2.22(m, 3H, ArCH$_3$)2.00(m, 1H) 1.85(m, 2H) 1.65, 1.52(3H, CH$_3$)1.30, 1.10(m, 1H)

(I-16)17.10(1H, OH)7.95(m, 1H, ArH)7.05(m, 1H, ArH) 3.35, 3.12(3H, OCH$_3$) 3.10(3H, SO$_2$CH$_3$)2.65(m, 3H, ArCH$_3$)2.20(s, 3H, ArCH$_3$)2.15(m, 2H) 1.62, 1.35(3H, CH$_3$)0.80(m, 1H)

(I-17) 7.95(m, 1H, ArH)7.12(m, 1H, ArH)4.07(m, 1H, ArOCH$_3$)3.53, 3.37(3H, OCH$_3$)3.26 (m, 3H, SO$_2$CH$_3$) 2.24 (m, 1H)1.90(m, 2H) 1.64, 1.52(3H, CH$_3$)1.13(m, 1H)

(I-18) 7.92(m, 1H, ArH)7.06(m, 1H, ArH)4.08(s, 3H, ArOCH$_3$) 3.32, 3.13(3H, OCH$_3$)3.27(s, 3H, SO$_2$CH$_3$)2.20 (m, 2H)1.68(m, 1H) 1.70, 1.37(3H, CH$_3$)0.82(m, 1H)

(I-19) 7.94(m, 1H, ArH)7.27(m, 1H, ArH)4.06(m, 3H, ArOCH$_3$) 3.69-3.40(m, 2H, OCH$_2$CH$_3$)3.26(s, 3H, SO$_2$CH$_3$)2.23(m, 6H)2.00-1.80(m, 2H)1.64, 1.52(3H, CH$_3$)1.20, 1.17(m, 4H)

(I-20) 7.93(m, 1H, ArH)7.10(m, 1H, ArH)4.07(s, 3H, ArOCH$_3$)3.42, 3.10(2H, OCH$_2$CH$_3$)3.28(s, 3H, SO$_2$CH$_3$) 2.20(m, 2H)1.67(m, 1H)1.68, 1.37(3H, CH$_3$) 1.15(m, 3H, OCH$_2$CH$_3$)

(I-22) 7.90(m, 1H, ArH)7.10(m, 1H, ArH)4.10(m, 5H)3.28 (m, 3H, SO$_2$CH$_3$) 2.20(m, 2H)1.70 (m, 1H)1.45, 1.25(3H, CH$_3$)0.85(m, 1H)

(I-24) 7.93(m, 1H, ArH)7.14(m, 1H, ArH)4.07(m, 1H, OCH$_3$)3.98, 3.84(1H, CH)3.44, 3.38(3H, SO$_2$CH$_3$)2.28 (m, 1H)2.03(m, 1H)1.83(m, 1H)1.63, 1.50(3H, CH$_3$) 1.34, 1.20(m, 6H, CH(CH$_3$)$_2$)

(I-25) 17.60(s, 1H, OH)7.85(d, 1H, ArH)6.95(d, 1H, ArH) 3.98(s, 3H, ArOCH$_3$)3.80(bs, 1H, OH)3.25(s, 3H, SO$_2$CH$_3$)2.25(m, 2H)2.24(s, 3H, ArCH$_3$)1.70(m, 1H)1.48 (s, 3H, CH$_3$)0.92(m, 1H)

(I-26)17.57(s, 1H, OH)7.81(d, 1HArH)6.99(d, 1H, ArH) 3.96(s, 3H, ArOCH$_3$) 3.24(s, 1H, SO$_2$CH$_3$)2.35(bs, 1H, OH)2.24(s, 3H, ArCH$_3$)2.17(m, 2H) 1.66(m, 1H)1.46(s, 3H, CH$_3$)0.80(m, 1H)

(I-27) 17.48(bs, 1H, OH)7.82(m, 1H, ArH)6.95(m, 1H, ArH)3.95(s, 3H, ArOCH$_3$)3.53, 3.38(3H, OCH$_3$)3.25(s, 3H, SO$_2$CH$_3$)2.22(m, 4H)1.85(m, 2H) 1.63, 1.51(3H, CH$_3$)1.20(m, 1H)

(I-28) 7.80(m, 1H, ArH)7.12(m, 1H, ArH)3.96(s, 3H, ArOCH$_3$) 3.48, 3.31, 3.11(3H, OCH$_3$)3.25(m, 3H, SO2CH$_3$)2.24-2.01(m, 4H)1.60(m, 2H) 1.66, 1.37(3H, CH$_3$)0.96-0.77(m, 1H)

(I-29) 17.58, 17.30(1H, OH)7.80(m, 1H, ArH)6.86(m, 1H, ArH)3.95(s, 3H, ArOCH$_3$) 3.57(m, 2H, OCH$_2$CH$_3$)3.22 (s, 3H, SO$_2$CH$_3$)2.23(m, 4H)1.90(m, 2H) 1.62, 1.51(3H, CH$_3$)1.25(m, 3H, OCH$_2$CH$_3$)1.12(m, 1H)

(I-30) 7.81(m, 1H, ArH)6.93(m, 1H, ArH)3.97(s, 3H, ArOCH$_3$)3.45, 3.04(2H, OCH$_2$CH$_3$)3.25(s, 3H, SO$_2$CH$_3$) 2.20(m, 4H)1.62(m, 1H)1.38, 1.25(3H, CH$_3$) 1.15(m, 3H, OCH$_2$CH$_3$)0.80(m, 2H)

(I-31) 17.60, 17.30(1H, OH)7.80(m, 1H, ArH)6.95(m, 1H, ArH)3.95(m, 1H, ArOCH$_3$) 3.90-3.26(m, 2H, CH$_2$CH$_2$CH$_3$)3.22(m, 3H, SO$_2$CH$_3$)2.22(m, 3H, ArCH$_3$) 2.10-1.50(m, 8H)1.38-1.04(m, 1H)1.02-0.83(m, 3H, CH$_2$CH$_3$)

(I-32) 17.60, 16.84(1H, OH)7.80(m, 1H, ArH)6.95(m, 1H, ArH)3.98(s, 3H, ArOCH$_3$)3.40-2.85(m, 2H, CH$_2$CH$_2$CH$_3$)3.25(s, 3H, SO$_2$CH$_3$)2.30-2.12(m, 1H) 2.22 (s, 3H, ArCH$_3$)1.70-1.38(m, 7H)0.93-0.72(m, 4H)

(I-33) 7.81(m, 1H, ArH)6.95(m, 1H, ArH) 3.95(m, 3H, ArOCH$_3$)3.82(m, 1H, CH) 3.24(s, 3H, SO$_2$CH$_3$)2.22(m, 3H, ArCH$_3$)2.10-1.92(m, 1H)1.90-1.65(m, 2H) 1.61, 1.50 (3H, CH$_3$)1.40-1.10(m, 7H)

(I-34) 7.82(m, 1H, ArH) 6.95(m, 1H, ArH)3.96(s, 3H, ArOCH$_3$)3.65(m, 1H, CH) 3.25(s, 3H, SO$_2$CH$_3$)2.23(m, 3H, ArCH$_3$ )2.20-1.85(m, 2H)1.78-1.48(m, 1H)1.65-1.40 (3H, CH$_3$)1.17-0.95(m, 6H, CH(CH$_3$)$_2$)0.92-0.70(m, 1H)

(I-35) 17.60, 17.26(bs, 1H, OH)7.81(m, 1H, ArH)6.95(m, 1H, ArH)6.10-5.86(m, 1H)5.43-5.11(m, 2H)4.40-3.92 (m, 2H, OCH$_2$)3.95(s, 3H, ArOCH$_3$) 3.24(s, 3H, SO$_2$ CH$_3$) 2.27, 2.22(s, 3H, ArCH$_3$)2.07-1.75 (m, 2H)1.69, 1.55(s, 3H, CH$_3$)1.43-1.13(m, 2H)

(I-36) 17.55, 16.88(bs, 1H, OH)7.77(m, 1H, ArH)6.92(m, 1H, Ar )5.90-5.70(m, 1H)5.30-5.10(m, 2H)3.96-3.52(m, 2H, OCH$_2$)3.95(s, 3H, ArOCH$_3$) 3.23(s, 3H, SO$_2$CH$_3$) 2.24, 2.21(s, 3H, ArCH$_3$)2.28-1.91(m, 1H)1.68, 1.39(s, 3H, CH$_3$)1.66-1.57 (m, 1H)0.90-0.72(m, 2H)

(I-37) 17.55(bs, 1H, OH)7.90(m, 1H, ArH)6.96(m, 1H, ArH)4.33(m, 2H, OCH$_2$) 3.96(s, 3H, ArOCH$_3$)3.25(s, 3H, SO$_2$CH$_3$)2.30(m, 5H)1.90(m, 2H) 1.68, 1.58(3H, CH$_3$) 1.12(m, 1H)

(I-38) 7.83(m, 1H, ArH)7.00(m, 1H, ArH)3.97(s, 3H, ArOCH$_3$)3.90(m, 2H, OCH$_2$) 3.26(s, 3H, SO$_2$CH$_3$)2.47(s, 1H, CH)2.22(m, 4H)1.66(m, 2H)1.43(s, 3H, CH$_3$)0.77(m, 1H)

(I-41) 17.42(bs, 1H, OH)7.92(m, 1H, ArH)7.13(m, 1H, ArH)6.54(d, J$_{HF}$=74Hz, 1H, CF$_2$H)3.53, 3.36(3H, OCH$_3$)3.22(s, 3H, SO$_2$CH$_3$)2.23(m, 4H)1.92(m, 2H) 1.64, 1.51(3H, CH$_3$)1.13(m, 1H)

(I-42) 17.49, 16.84(1H, OH)7.91(m, 1H, ArH)7.13(m, 1H, ArH)6.56(d, J$_{HF}$=75Hz, 1H, CF$_2$H)3.31, 3.11(3H, OCH$_3$)

3.24(s, 3H, SO₂CH₃)2.29(s, 3H, ArCH₃) 2.17(m, 1H)1.67 (m, 1H)1.66, 1.37(3H, CH₃)0.79(m, 1H)

(I-43) 17.58, 17.28(bs, 1H, OH)7.84, 7.81(d, 1H, ArH)6.98, 6.93(d, 1H, ArH) 3.97, 3.95(s, 3H, ArOCH₃)3.90-3.35(m, 2H)3.24(s, 3H, SO₂CH₃) 2.26, 2.21(s, 3H, ArCH₃)2.30-1.25(m, 7H) 1.62, 1.50(s, CH₃)1.12, 0.95(m, 1H) 0.98, 0.88(t, 3H)

(I-44) 17.60, 16.93(bs, 1H, OH)7.83, 7.80(d, 1H, ArH)6.96, 6.92(d, 1H, ArH) 3.97(s, 3H, ArOCH₃)3.38, 2.97(m, 2H)3.25(s, 3H, SO₂CH₃)2.26, 2.22(s, 3H, ArCH₃) 2.28-1.90 (m, 2H)1.65, 1.36(s, 3H, CH₃) 1.65-1.23 (m, 4H)0.91(t, 3H) 1.86, 0.77(m, 1H)

(I-45) 17.60, 17.27(bs, 1H, OH)7.80(m, 1H, ArH)6.95(m, 1H, ArH) 3.95(s, 3H, ArOCH₃)3.61-3.26(m, 2H, OCH₂) 3.23(s, 3H, SO₂CH₃)2.27, 2.22(s, 3H, ArCH₃)2.03-1.74 (m, 3H)1.62, 1.51(s, 3H, CH₃)1.54(m, 1H)1.31-1.07(m, 1H) 1.02-0.83(m, 6H, CH₃)0.53(m, 2H)0.13(m, 1H)

(I-46) 17.62, 16.94 (bs, 1H, OH)7.80(m, 1H, ArH)6.94(m, 1H, ArH) 3.96(s, 3H, ArOCH₃)3.25(s, 3H, SO₂CH₃)3.18-2.82(m, 2H, OCH₂)2.24, 2.22(s, 3H, ArCH₃)2.17(m, 1H)1.75(m, 1H)1.65, 1.37(s, 3H, CH₃)1.62(m, 1H)0.92-0.76(m, 8H)

(I-48) 17.60, 16.89(bs, 1H, OH)7.80(d, 1H, ArH)6.93(d, 1H, ArH) 3.96(s, 3H, ArOCH₃)3.25(s, 3H, SO₂CH₃)3.16-2.87 (m, 2H, OCH₂)2.25, 2.22(s, 3H, ArCH₃)2.20-1.89(m, 1H)1.66, 1.35(s, 3H, CH₃)1.62(m, 1H)1.01-0.83(m, 1H) 0.77(m, 1H)0.53(m, 2H)0.13(m, 1H)

(I-49) 17.62, 17.35(bs, 1H, OH)7.85(m, 1H, ArH)7.52-7.20 (m, 5H, PhH) 6.96(m, 1H, ArH)4.90-4.52(m, 2H, CH₂Ph) 3.98(s, 3H, ArOCH₃)3.25(s, 3H, SO₂CH₃) 2.27, 2.24(s, 3H, ArCH₃)2.11-1.72(m, 2H)1.71, 1.60(s, 3H, CH₃ )1.44-1.17(m, 2H)

(I-50) 7.80(m, 1H, ArH)6.95(m, 1H, ArH)4.20-3.95(m, 1H, OCH)3.97(s, 3H, ArOCH₃) 3.25(s, 3H, SO₂CH₃)2.27, 2.22(s, 3H, ArCH₃)2.08-1.35(m, 11H)1.63, 1.51(s, 3H, CH₃)1.16(m, 1H)

(I-51) 7.81(m, 1H, ArH)6.97(m, 1H, ArH)4.32-3.80(m, 1H, OCH)3.99(s, 3H, ArOCH₃) 3.26(s, 3H, SO₂CH₃)2.26(s, 3H, ArCH₃)2.27-1.88(m, 1H )1.82-1.25(m, 10H) 1.64, 1.37(s, 3H, CH₃)0.90-0.72(m, 1H)

(I-53) 17.68, 16.91(bs, 1H, OH)7.80(m, 1H, Arh)6.94(m, 1H, ArH)4.10-3.68(m, 2H, CH₂Ac)3.97(s, 3H ,ArOCH₃) 3.26(s, 3H, SO₂CH₃)2.31-2.09(m, 8H) 1.70, 1.38(s, 3H, CH₃)1.71-1.25(m, 1H)0.95-0.76(m, 1H)

(I-54) 17.58, 17.23(bs, 1H, OH)7.81(m, 1H, ArH)6.95(m, 1H, ArH)4.10-3.58(m, 4H)3.95(s, 3H, ArOCH₃)3.23 (s, 3H, SO₂CH₃)2.25(m, 1H) 2.25, 2.22(s, 3H, ArH)2.07-1.78(m, 1H)1.65, 1.55(s, 3H, CH₃)1.33-1.06(m, 1H)

(I-55) 17.67, 16.95(bs, 1H, OH)7.81(m, 1H, ArH)6.98(m, 1H, ArH) 3.97(s, 3H, ArOCH₃)3.80-3.52 (m, 4H)3.22(s, 3H, SO₂CH₃)2.30-1.85(m, 2H) 2.23(s, 3H, ArH)1.70, 1.40(s, 3H, CH₃)1.68-1.54(m, 1H)0.90-0.76(m, 1H)

(I-56) 17.55, 17.23(bs, 1H, OH)7.80(m, 1H, ArH)6.95(m, 1H, ArH)4.30-4.06(m, 1H)3.95(s, 3H, ArOCH₃)3.90-3.45 (m, 3H)3.24(s, 3H, S₂CH₃) 2.45, 2.22(s, 3H, ArH)2.30-2.10(m, 1H)2.05-1.76(m, 2H)1.64, 1.53(s, 3H, CH₃)1.34-1.25(m, 1H)

(I-57) 17.65, 16.96(bs, 1H, OH)7.82(d, J=8.1Hz, 1H, ArH) 7.02(d, J=8.1Hz, 1H, Arh) 3.97(s, 3H, ArOCH₃)3.81-3.69 (m, 2H)3.42-3.21(m, 2H)3.26(s, 3H, SO₂CH₃)2.27-1.92 (m, 2H)2.26, 2.23(s, 3H, ArH)1.69, 1.40(s, 3H, CH₃)1.67-1.60(m, 1H) 0.92-0.76(m, 1H)

(I-58) 17.58, 17.20(bs, 1H, OH)7.82(m, 1H, ArH)6.95(m, 1H, ArH)4.13-3.62(m, 2H)3.96(s, 3H, ArOCH₃)3.24(s, 3H, SO₂CH₃)2.77-2.56(m, 2H)2.30-2.16(m, 1H)2.26, 2.21(s, 3H, ArH)2.08-1.79(m, 2H)1.66, 1.55(s, 3H, CH₃) 1.32-1.07(m, 1H)

(I-59) 17.67, 16.93(bs, 1H, OH)7.80(d, J=7.5Hz, 1H, ArH) 7.02(d, J=7.5Hz, 1H, ArH)3.97(s, 3H, ArOCH₃)3.62-3.20 (m, 2H)3.23(s, 3H, SO₂CH₃)2.55(m, 2H)2.30-1.95(m, 2H)2.25, 2.21(s, 3H, ArH)1.70, 1.40(s, 3H, CH₃)1.65(m, 1H)0.93-0.77(m, 1H)

(I-60) 17.62, 16.87(bs, 1H, OH)7.80(m, 1H, ArH)7.00(m, 1H, ArH) 3.95(s, 3H, ArOCH₃)3.68(m, 2H, CH₂OH)3.52-3.05(m, 2H, OCH₂)3.25(s, 3H, SO₂CH₃)2.26, 2.24(s, 3H, ArCH₃)2.16(m, 2H)2.10-1.75(m, 2H)1.68, 1.40(s, 3H, CH₃) 1.66(m, 1H)0.96-0.77(m, 1H)

(I-62)17.76, 17.23(bs, 1H, OH)8.10, 8.00(s, 1H, CHO)7.85, 7.82(d, 1H, ArH) 7.05, 6.96(d, 1H, ArH)3.97, 3.96(s, 3H, ArOCH₃)2.40-1.70(m, 3H)3.24(s, 3H, SO₂CH₃)2.26, 2.23(s, 3H, ArCH₃)1.80, 1.71(s, CH₃)1.61, 1.52(m, 1H)

(I-64) 17.78, 17.29(bs, 1H, OH)7.83, 7.80(d, 1H, ArH)7.05, 6.96(d, 1H, ArH) 3.95, 3.93(s, 3H, ArOCH₃)3.24(s, 3H, SO₂CH₃)2.36, 2.21(s, 3H, ArCH₃)2.30-1.40 (m, 4H)2.18, 2.15(s, 3H, COCH₃)1.75, 1.64(s, CH₃)

(I-65) 17.42(s, 1H, OH)7.80(d, 1H, ArH)6.98(d, 1H, ArH 3.93(s, 3H, ArOCH₃)3.24(s, 3H, SO₂CH₃)2.43(m, 1H)2.20(m, 1H)2.21(s, 3H, ArCH₃)2.03(s, 3H, COCH₃) 1.62(m, 1H)1.60(s, 3H, CH₃)0.87(m, 1H)

(I-66) 7.83, 7.78(d, 1H, ArH)7.03, 6.96(d, 1H, ArH)3.95, 3.93(s, 3H, ArOCH₃)3.24(s, 3H, SO₂CH₃)2.26, 2.21(s, 3H, ArCH₃)2.60-1.40(m, 6H)1.74, 1.63(s, CH₃) 1.18, 1.08(t, 3H)

(I-67) 7.83(d, 1H, ArH)6.98(d, 1H, ArH)3.95(s, 3H, ArOCH₃)3.25(s, 3H, SO₂CH₃)2.46(m, 1H)2.32(q, 2H)2.30(m, 1H)2.24(s, 3H, ArCH₃)1.62(s, 3H, CH₃) 1.16 (m, 1H)1.12(t, 3H)0.91(m, 1H)

(I-68) 17.81, 17.30(bs, 1H, OH)8.15-7.35(m, 6H, ArH)7.08, 7.00(d, 1H, ArH) 3.97, 3.93(s, 3H, ArOCH₃)3.26, 3.22(s, 3H, SO₂CH₃)2.40-1.50(m,4H) 2.30, 2.25(s, 3H, ArCH₃) 1.92, 1.18(s, CH₃)

(I-69) 17.43(s, 1H, OH)7.97(d, 2H, ArH)7.85(d, 1H, Ar)7.61 (m, 1H, Ar) 7.47(m, 2H, Ar)7.02(d, 1H, ArH)3.96(s,3H, ArOCH₃)3.25(s, 3H, SO₂CH₃) 2.57(m, 1H)2.32(m, 1H)2.23(s, 3H, ArCH₃)1.76(s, 3H, CH₃)1.70(m, 1H) 1.00 (m, 1H)

(I-70) 17.60, 17.35(bs, 1H, OH)7.76(m, 2H, ArH)7.27, 7.16(m, 1H, ArH) 3.53, 3.34(s, 3H, OCH₃)3.07, 3.04(s, 3H, SO₂CH₃)2.35, 2.32(s, 3H, ArCH₃) 2.28, 1.96(m , 1H)1.95, 1.53(m, 1H)1.81(m, 1H)1.60, 1.50(s, 3H, CH₃) 1.35, 1.05(m, 1H)

(I-71) 17.65, 17.00(bs, 1H, OH)7.76(m, 2H, ArH)7.24(m, 1H, ArH) 3.30, 3.10(s, 3H, OCH₃)3.05(s, 3H, SO₂CH₃) 2.36, 2.33(s, 3H, ArCH₃) 1.65, 1.36(s, 3H, CH₃)0.93, 0.74(m, 1H)

(I-74) 17.00, 16.91(bs, 1H, OH)7.96(m, 1H, ArH)7.61(m, 1H, ArH) 7.37, 7.11(m, 1H, ArH)3.51, 3.34(s, 3H, OCH₃) 3.14(s, 3H, SO₂CH₃)2.20(m, 1H) 1.86(m, 2H)1.65, 1.48 (s, 3H, CH₃)1.43, 1.10(m, 1H)

(I-75) 17.08, 16.60(bs, 1H, OH)8.00(m, 1H, ArH)7.60 (m, 1H, ArH) 7.27, 7.08 (m, 1H)3.62, 3.31(s, 3H, OCH₃)3.15, 3.14(s, 3H, SO₂CH₃)2.16(m, 1H)1.64 (m, 2H)1.79, 1.35 (s, 3H, CH₃)0.95, 0.77(m, 1H)

(I-76) 7.92(m, 1H, ArH)7.00(m, 1H, ArH)3.25(m, 6H)2.25 (bs, 3H, ArCH₃) 1.91(1H )1.79(m, 1H)1.58(m, 1H)1.37(s, 3H, CH₃)1.12, 0.76(m, 1H)

(I-77) 17.50(bs, 1H, OH)8.07(m, 1H, ArH)7.16(m, 1H, ArH)3.33(s, 3H, SO₂CH₃). 10(s, 3H, OCH₃)2.39(bs, 3H, ArCH₃)2.23(m, 1H)2.15(m, 1H)1.66(m, 1H) 1.36(s, 3HH₃)0.74, 1.60(m, 1H)

(I-78) 17.32, 17.03(bs, 1H, OH)7.72, 7.69(d, 1H, ArH)7.11, 6.98(d, 1H, ArH) 4.01(s, 3H, ArOCH₃)4.01(s, 3H, ArOCH₃)3.93, 3.90(s, 3H, ArOCH₃)3.52, 3.35(s, 3H, OCH₃)3.24, 3.23(s, 3H, SO₂CH₃)2.30-1.70(m, 3H)1.61, 1.53(s, SH, CH₃)1.35, 1.08(m, 1H)

(I-79) 17.47, 16.63(bs, 1H, OH)7.72, 7.69(d, 1H, ArH)7.12, 6.93(d, 1H, ArH) 4.04, 4.00(s, 3H, ArOCH$_3$)3.99, 3.97(s, 3H, ArOCH$_3$)3.30, 3.17(s, 3H, OCH$_3$)3.27(s, 3H, SO$_2$CH$_3$)2.30-1.35(m, 3H)1.66, 1.39(s, 3H, CH$_3$)0.93, 0.77(m, 1H)

(I-80) 17.20(bs, 1H, OH)7.93(m, 1H, ArH)7.09(m, 1H, ArH)4.08(s, 3H, OCH$_3$) 3.26(s, 3H, SO$_2$CH$_3$)2.35-2.10 (m, 2H)1.72(m, 1H)1.71, 1.50(s, 3H, CH$_3$)0.93(m, 1H)

(I-81) 7.90 (m, 1H, ArH)7.10(m, 1H, ArH)4.07(s, 3H, OCH$_3$)3.26(s, 3H, SO$_2$CH$_3$) 2.35-1.40 (m, 3H)1.69, 1.44 (s, 3H, CH$_3$)0.94, 0.82 (m, 1H)

(I-82) 7.93(m, 1H, ArH)7.12(m, 1H, ArH)4.05(bs, 3H, OCH$_3$)3.87-3.25(m, 2H) 3.25(s, 3H, SO$_2$CH$_3$)2.35-1.20 (m, 5H)1.64, 1.52(s, 3H, CH$_3$)1.15-0.80(m, 1H) 1.01, 0.89(t, 3H, CH$_3$)

(I-83) 7.92 (m, 1H, ArH)7.18, 7.02 (m, 1H, ArH)4.09, 4.07(s, 3H, OCH$_3$)3.28(s, 3H, SO$_2$CH$_3$)3.45-2.90(m, 2H)2.30-2.00(m, 2H)1.75-1.20(m, 3H)1.67, 1.38(s, 3H, CH$_3$) 1.00-0.75(m, 4H)

(I-84) 7.93(m, 1H, ArH)7.12(m, 1H, ArH)4.08, 4.04(br, 3H, OCH$_3$)3.90-3.25(m, 2H)3.27(s, 3H, SO$_2$CH$_3$)2.30-1.20 (m, 15H)1.63, 1.53(s, 3H, CH$_3$)1.20-0.80(m, 4H)

(I-85) 7.93(m, 1H, ArH)7.24-6.94(m, 1H, ArH)4.08(s, 3H, OCH$_3$) 3.27(s, 3H, SO$_2$CH$_3$)3.50-2.90(m, 2H)2.30-1.10 (m, 15H)1.67, 1.37(s, 3H, CH$_3$)0.97-0.74(m, 4H)

(I-86) 17.3, 16.0(bs, 1H, OH)8.11, 8.00(s, 1H, COH)7.94(m, 1H, ArH)7.22 -7.05(m, 1H, ArH)4.06(s, 3H, OCH$_3$)3.25 (s, 3H, SO$_2$CH$_3$)2.4-1.6(m, 3H) 1.82, 1.73(s, 3H, CH$_3$) 1.14-0.95(m, 1H)

(I-87) 17.12(bs, 1H, OH)7.95(s, 1H, COH)7.92(d, J=8.03Hz, 1H, ArH)7.08(d, J=8.03Hz, 1H, ArH)4.08(s, 3H, OCH$_3$)3.26(s, 3H, SO$_2$CH$_3$)2.50(m, 1H)2.29(m, 1H) 1.72(m, 1H)1.68(s, 3H, CH$_3$)0.94(m, 1H)

(I-90) 7.67(m, 1H, ArH)6.82(m, 1H, ArH)3.90(s, 3H, OCH$_3$)3.41(s, 3H, OCH$_3$) 3.22(s, 3H, SO$_2$CH$_3$)2.23(s, 3H, ArCH$_3$)1.83(m, 1H)1.59(m, 1H)1.40(s, 3H, CH$_3$) 1.31(m, 1H)1.02(m, 1H)

(II-1) 17.50(s, 1H, OH)7.95(m, 1H, PyH)7.60(m, 1H, PyH) 3.52, 3.38(m, 3H, OCH$_3$) 3.22(m, 3H, SO$_2$CH$_3$)2.53(m, 3H, PyCH$_3$)2.22(m, 2H)1.60(m, 1H) 1.63, 1.50(3H, CH$_3$) 1.16(m, 1H)

(II-2) 17.64, 16.70(1H, OH)7.95(m, 1H, PyH) 7.60(m, 1H, PyH) 3.33, 3.10(3H, OCH$_3$) 3.25(s, 3H, SO$_2$CH$_3$)2.55(m, 3H, PyCH$_3$)2.20(m, 2H)1.63(m, 1H) 1.65, 1.39(3H, CH$_3$) 0.80(m, 1H)

(II-27) 7.85, 7.80(d, 1H, ArH)6.99, 6.91(d, 1H, ArH)3.97, 3.95(s, 3H, ArOCH$_3$)3.53, 3.35(s, 3H, OCH$_3$)3.27, 3.25(s, 3H, SO$_2$CH$_3$)2.26, 2.24(s, 3H, ArCH$_3$) 1.01, 0.85(t, CH$_3$) 2.50-1.80(m, 1H)

(II-31) 7.83, 7.79(d, 1H, ArH)6.97, 6.92(d, 1H, ArH)3.96, 3.94(s, 3H, ArOCH$_3$)3.30-3.80(m, 2H)3.24(s, 3H, SO$_2$CH$_3$)2.24, 2.22(s, 3H, ArCH$_3$)1.28, 1.12(m, 1H) 1.02, 0.89(t, 3H)

(II-32) 7.82, 7.80(d, 1H, ArH)6.96, 6.91(d, 1H, ArH)3.97(s, 3H, ArOCH$_3$) 3.32, 2.85(m, 2H)3.26, 3.24(s, 3H, SO$_2$CH$_3$)2.26, 2.24(s, 3H, ArCH$_3$)2.30-0.70(m, 8H)1.12, 0.95(t, 3H)10.88(t, 3H)

The compounds according to the present invention represented by the general formula [I] and the salts thereof provide an high herbicidal activity in fields of upland crops by either method of soil application or foliar application. For example, the compounds according to the present invention show to have an excellent herbicidal activity by means of foliar application to hazardous weeds in upland crop fields, such as crabgrass, foxtails, velvet leaf, pigweed, cocklebur etc., and some of such compounds show to have selectivity in their herbicidal activity between weeds and crops, which are not toxic to crops, such as maize, cereals, soybeans, cotton plant, etc. In particular, the compounds according to the present invention have an excellent herbicidal activity against hazardous weeds, such as foxtails, pigweed and cocklebur in maize cultivation so that the compounds are very uszful as the active one of herbicide for weed control in maize fields.

Further, in the compounds of the present invention, compounds which have a growth-regulating activity against useful plants, such as agricultural crops, ornamental plants and fruit trees, are contained as well.

Moreover, the compounds of the present invention show to have an excellent herbicidal activity against weeds grown in paddy rice fields, such as barnyardgrass, umbrella plants (Cyperus difformis and Scirpus juncoides) and water plantains, and some of the compounds have selectivity in their herbicidal activity between such weeds and rice plants.

Furthermore, the compounds according to the present invention can be also applied for weed control in orchards, lawns, areas along the side of railways, vacant lands, etc.

The compounds according to the present invention are low toxic to both fishes and homeothermal animals, and are therefore considered as highly safe chemicals.

[Herbicides]

The herbicide according to the present invention comprises one or more of the compounds according to the present invention as the active ingredient(s). At a practical application of the inventive compounds, such compounds can be applied without combining with other elements. Alternatively, such inventive compounds can be also prepared into any of formulation types to be normally employed as plant protection chemicals, such as wettable powder, granules, dust, emulsifiable concentrate, water soluble powder, suspension and flowable formulations. As an additive or a filler used for such formulations, vegetable-origin powder, such as soybean powder and wheat flour, mineral fine powder, such as diatomaceous earth, apatite, gypsum, talc, bentonite, pyrophyllite and clay, and organic or inorganic materials, such as sodium benzoate, urea and Glauber's salt, can be used for a solid-type formulation. In case liquid-type formulations are required, a petroleum fraction, such as kerosine, xylene and solvent naphtha, cyclohexane, cyclohexanone, dimethyl formamide, dimethyl sulfoxide, alcohol, acetone, methylisobutyl ketone, mineral oil, vegetable oil, water, etc. can be used as a solvent. In order to assure uniform and stable physicochemical properties for such formulations, a surface active agent may be used, if appropriate.

The content or the concentration of active ingredient contained in the herbicide according to the present invention can differ to various ranges depending upon formulation types as described above. For example, such content can be in a range of from 5 to 90%, and preferably of from 10 to 85%, for a wettable powder formulation; from 3 to 70%, and preferably of from 5 to 30%, for an emulsifiable concentrate formulation; and from 0.01 to 30%, and preferably of from 0.05 to 10%, for a granular formulation.

The wettable powder and the emulsifiable concentrate obtained as described above can be applied in a form of suspension or emulsion after diluting such formulations with appropriate volume of water. The granules obtained as described above can be applied to and/or incorporated into soil without dilution prior to or after germination of weeds. For practical application of the herbicide according to the present invention, a formulation wherein the compound of the present invention is contained as the active ingredient is applied at an appropriate dose more than 0.1 g/10 a based said active ingredient.

The herbicide according to the present invention can be also used by a mixing with any of other known fungicides, insecticides, acaricides, herbicides, plant growth regulators, etc. In particular, it is possible to reduce the dose of the active ingredient in the inventive herbicide in practical uses owing to a mixing with other herbicide. In this case, such mixing may provide an effect not only to reduce labours required for weeding but also to give higher herbicidal performance because of a synergistic action brought by both herbicides mixed together. It is also possible to make combinations with the inventive herbicidal compound and a plurality of other known herbicides.

For the examples of herbicides to be preferably associated with the inventive herbicide, carbamate herbicides, such as benthiocarb, molinate and dimepiperate, thiocarbamate herbicides, acid amide herbicides, such as butachlor, pretilachlor and mefenacet, diphenyl ether herbicides, such as chlomethoxynil and bifenox, triazine herbicides, such as atrazine and cyanazine, sulfonylurea herbicides, such as chlorsulfuron and sulfometuron-methyl, phenoxyalkanebarboxylic acid herbicides, such as MCP, and MCPB, phenoxyphenoxypropionic acid herbicides such as diclofop-methyl, pyridyloxyphenoxypropionic acid herbicides such as fluazifop-butyl, dinitroaniline herbicides, such as trifluralin and pendimethalin, urea herbicides, such as linuron and diuron, benzoylaminopropionic acid herbicides, such as benzoylprop ethyl and furanprop ethyl, imidazolinone herbicides such as imazaquin, and others, such as piperophos, dymron, bentazone, difenzoquat, naproanilide, etobenzanid, triazofenamide, quinclorac, and cyclohexanedione herticides. such as sethoxydim and clethodim, can be given. In addition, a vegetable oil and an oil concentrate may be added to a combination consisting of the inventive herbicide and one or more of the herbicides exemplified above.

[Herbicides]

Now, examples for manufacturing formulations suitable for the herbicide according to present invention are given hereinbelow. However, a compound to be used as an active component, types of additives and additional portions of the additives to use shall be modified in wide ranges and shall not be limited to the ones specified in the examples described hereinbelow. The part described in the following Examples represent parts by weight based on the weight of the formulation.

(EXAMPLE 6)
Wettable Powder

| The inventive compound | 20 parts |
|---|---|
| White carbon | 20 parts |
| Diatomaceous earth | 52 parts |
| Sodium alkylsulfate | 8 parts |

All materials are uniformly mixed and grinded into fine powders to obtain a wettable powder formulation comprising an active ingredient at a content of 20%.

(EXAMPLE 7)
Emulsifiable Concentrate

| The inventive compound | 20 parts |
|---|---|
| Xylene | 55 parts |
| Dimethylformamide | 15 parts |
| Polyoxyethylene phenyl ether | 10 parts |

All materials are mixed and dissolved to obtain an emulsifiable concentrate formulation comprising an active ingredient at a content of 20%.

(EXAMPLE 8)
Granules

| The inventive compound | 5 parts |
|---|---|
| Talc | 40 parts |
| Clay | 38 parts |
| Bentonite | 10 parts |
| Sodium alkylsulfate | 7 parts |

All materials are uniformly mixed, grinded to fine powders and then granulated into granules having a diameter of from 0.5 to 1.0 mm to obtain a granular formulation comprising an active ingredient at a content of 5%.

A test example carried out to show a herbicidal activity of the herbicides according to the present invention are now described hereinbelow.

However, the herbicidal activity as described hereinbelow is evaluated pursuant to the following criterion, and therefore, the herbicidal activity is expressed as an index for killed-weeds.

| Criterion for assessment | |
|---|---|
| % of weeds killed | Index for killed-weeds |
| 0% | 0 |
| 20–29% | 2 |
| 40–49% | 4 |
| 60–69% | 6 |
| 80–89% | 8 |
| 100% | 10 |

Indexes 1, 3, 5, 7 and 9 represent an intermediate activity between 0 and 2, 2 and 4, 4 and 6, 6 and 8, and 8 and 10, respectively.

% of Weeds Killed [(Weight of fresh weeds growing over the ground in non-treated plot−Weight of fresh weeds growing over the ground in a treated-plot)÷(Weight of fresh weeds growing over the ground in non-treated plot)]×100

(Test Example 1) Foliar application

In a 200 cm$^2$ planting pot filled with soil beforehand, seeds of giant foxtail, pigweed, cocklebur and maize are respectively planted, and the seeds are then covered with a slight amount of soil to grow in a greenhouse. When each of such weeds and maize have grown to a height of 5 to 10 cm and at 20 cm height, respectively, a water emulsion prepared with an emulsifiable concentrate prepared for the test compound was applied by using a small sprayer to the leaves of the weeds and maize at a dose rate specified in Table 5 and with a spray volume rate of 100 liters/10 a. Three weeks later, the herbicidal performance of the compounds were respectively assessed pursuant o the criterion as described above, and the results are presented in Tables 3 and 4 described below.

TABLE 5

| Compound No. | Dose g/10a | Index for Killed-Weeds | | | |
|---|---|---|---|---|---|
| | | Giant foxtail | Pigweed | Cocklebur | Maize |
| I-2 | 12.5 | 10 | 10 | 10 | 3 |
| I-3 | 12.5 | 10 | 10 | 10 | 0 |
| I-4 | 12.5 | 10 | 10 | 10 | 4 |
| I-8 | 12.5 | 10 | 10 | 10 | 0 |
| I-13 | 12.5 | 10 | 10 | 10 | 0 |
| I-14 | 12.5 | 10 | 10 | 10 | 0 |
| I-16 | 12.5 | 10 | 10 | 10 | 0 |
| I-17 | 12.5 | 10 | 10 | 10 | 0 |

TABLE 5-continued

| Compound No. | Dose g/10a | Index for Killed-Weeds | | | |
|---|---|---|---|---|---|
| | | Giant foxtail | Pigweed | Cocklebur | Maize |
| I-18 | 12.5 | 10 | 10 | 10 | 0 |
| I-19 | 12.5 | 10 | 10 | 10 | 0 |
| I-20 | 12.5 | 10 | 10 | 10 | 0 |
| 1-22 | 12.5 | 10 | 10 | 10 | 0 |
| I-24 | 12.5 | 10 | 10 | 10 | 0 |
| I-25 | 12.5 | 10 | 10 | 8 | 0 |
| I-26 | 12.5 | 10 | 10 | 9 | 0 |
| I-27 | 12.5 | 10 | 10 | 10 | 0 |
| I-28 | 12.5 | 10 | 10 | 10 | 0 |
| I-29 | 12.5 | 10 | 10 | 10 | 0 |
| I-30 | 12.5 | 10 | 10 | 10 | 0 |
| I-31 | 12.5 | 10 | 10 | 10 | 0 |
| I-32 | 12.5 | 10 | 10 | 10 | 0 |
| I-33 | 12.5 | 10 | 10 | 10 | 0 |
| I-34 | 12.5 | 10 | 10 | 10 | 0 |
| I-36 | 12.5 | 10 | 9 | 9 | 0 |
| I-37 | 12.5 | 10 | 10 | 10 | 0 |
| I-38 | 12.5 | 10 | 10 | 10 | 0 |
| 1-40 | 12.5 | 10 | 10 | 10 | 0 |
| I-41 | 12.5 | 10 | 10 | 10 | 0 |
| I-42 | 12.5 | 10 | 10 | 10 | 0 |
| I-44 | 12.5 | 10 | 9 | 9 | 3 |
| I-46 | 12.5 | 10 | 9 | 10 | 0 |
| I-48 | 12.5 | 10 | 10 | 10 | 0 |
| I-53 | 6.25 | 10 | 7 | 9 | 0 |
| I-55 | 12.5 | 10 | 9 | 9 | 0 |
| I-59 | 12.5 | 9 | 9 | 9 | 0 |
| I-60 | 12.5 | 9 | 8 | 9 | 0 |
| 1-62 | 12.5 | 10 | 10 | 9 | 0 |
| I-64 | 6.25 | 10 | 9 | 9 | 0 |
| I-65 | 6.25 | 10 | 10 | 9 | 0 |
| I-69 | 12.5 | 9 | 10 | 9 | 0 |
| I-70 | 12.5 | 10 | 10 | 8 | 0 |
| I-74 | 12.5 | 9 | 10 | 10 | 4 |
| I-77 | 12.5 | 10 | 9 | 9 | 0 |
| I-81 | 12.5 | 10 | 10 | 10 | 2 |
| I-83 | 12.5 | 10 | 10 | 10 | 2 |
| I-90 | 12.5 | 10 | 10 | 10 | 0 |
| II-27 | 12.5 | 10 | 9 | 8 | 0 |
| II-31 | 12.5 | 10 | 10 | 8 | 0 |
| IV-2 | 12.5 | 10 | 10 | 10 | 0 |
| Compound A | 12.5 | 5 | 10 | 10 | 0 |

Compound A (For comparison)

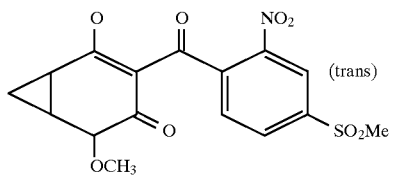

Industrial Use of the Invention

As explained above, substituted-bicycloheptanedione derivatives and the salts thereof according to the present invention are hating an excellent herbicidal activity, and herbicides comprising tie said compounds and the salts as the active component(s) are considered as an useful herbicide.

What is claimed is:

1. Substituted bicycloheptanedione derivatives represented by the formula [I];

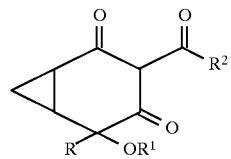

wherein R represents a $C_1$–$C_4$ alkyl, $R^1$ represents hydrogen, a $C_1$–$C_{10}$ alkyl, a $C_2$–$C_4$ alkenyl, a $C_2$–$C_4$ alkynyl, an aralkyl, a $C_2$–$C_4$ haloalkynyl, a $C_1$–$C_4$ alkoxy $C_1$–$C_4$ alkyl, a $C_1$–$C_4$ haloalkyl, a $C_2$–$C_4$ haloalkenyl, a hydroxy $C_1$–$C_4$ alkyl, a —A—$C_3$–$C_6$ cycloalkyl, —A—C(O)r, —A—$CH_2CN$ or phenyl, A represents a single bond or $C_1$–$C_4$ alkylene, r represents hydrogen, a $C_1$–$C_4$ alkyl, a $C_1$–$C_4$ alkoxy or phenyl, and $R^2$ represents optionally substituted phenyl or optionally substituted pyridyl, and the salts thereof.

2. (Amended) Substituted bicycloheptanedione derivatives represented by the formula (II):

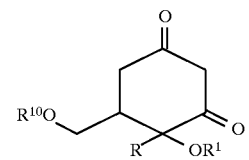

wherein R represents a $C_1$–$C_4$ alkyl, $R^1$ represents hydrogen, a $C_1$–$C_{10}$ alkyl, a $C_2$–$C_4$ alkenyl, a $C_2$–$C_4$ alkynyl, an aralkyl, a $C_2$–$C_4$ haloalkynyl, a $C_1$–C4 alkoxy $C_1$–$C_4$ alkyl, a $C_1$–$C_4$ haloalkyl, a $C_2$–$C_4$ haloalkenyl, a hydroxy $C_1$–$C_4$ alkyl, a —A—$C_3$–$C_6$ cycloalkyl, —A—C(O)r, —A—$CH_2CN$ or phenyl, A represents a single bond or $C_1$–$C_4$ alkylene, r represents hydrogen, a $C_1$–$C_4$ alkyl, a $C_1$–$C_4$ alkoxy or phenyl, and $R^{10}$ represents a $C_1$–$C_4$ alkyl, an aralkyl or acetyl.

3. A herbicidal composition comprising a herbicidally effective amount of a substituted bicycloheptanedione derivative according to claim 1.

4. Substituted bicycloheptanedione derivatives represented by the formula (I):

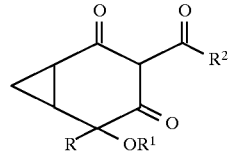

wherein R represents a $C_1$–$C_4$ alkyl, $R^1$ represents hydrogen, a $C_1$–$C_4$ alkyl, a $C_2$–$C_4$ alkenyl, a $C_2$–$C_4$ alkynyl, a $C_1$–$C_4$ alkoxy $C_1$–$C_4$ alkyl, a $C_1$–$C_4$ haloalkyl, a $C_2$–$C_4$ haloalkenyl, a $C_1$–$C_4$ alkylcarbonyl-$C_1$–$C_4$ alkyl, a $C_1$–$C_4$ alkylcarbonyl, a $C_1$–$C_4$ alkoxycarbonyl-$C_1$–$C_4$ alkyl, a $C_1$–$C_4$ alkoxycarbonyl, a benzoyl, a benzoyl-$C_1$–$C_4$ alkyl or formyl, $R^2$ is a phenyl which is substituted by halogen, $C_1$–$C_5$ alkyl, $C_1$–$C_4$ haloalkyl, $C_1$–$C_4$ alkoxy, $C_1$–$C_4$ haloalkoxy, $C_2$–$C_4$ alkenyloxy, $C_2$–$C_4$ alkynyloxy, $C_2$–$C_4$ haloalkenyloxy, $C_1$–$C_4$ alkoxy-$C_1$–$C_4$ alkyl, $C_1$–$C_4$ alkoxy-$C_1$–$C_4$ alkoxy, nitro, $C_1$–$C_4$ alkoxycarbonyl, $C_1$–$C_4$ alkylthio, $C_1$–$C_4$ alkylsulfinyl, $C_1$–$C_4$ alkylsulfonyl, $C_2$–$C_4$ alkenyl, $C_2$–$C_4$ haloalkenyl, $C_1$–$C_4$ alkylthio-$C_1$–$C_4$ alkyl, $C_1$–$C_4$ alkylsulfonyl-$C_1$–$C_4$ alkyl, $C_1$–$C_4$-alkylsulfinyl-$C_1$–$C_4$ alkyl, $C_1$–$C_4$ dialkylaminosulfonyl, carbamoyl, $C_1$–$C_4$ alkylcarbamoyl, $C_1$–$C_4$ dialkylcarbamoyl, carboxy, $C_1$–$C_4$ alkylcarbonyl, hydroxy, cyano, $C_2$–$C_4$ alkenylthio, $C_2$–$C_4$ alkenylsulfinyl, $C_2$–$C_4$ alkenylsulfonyl, $C_2$–$C_4$ alkynylthio, $C_2$–$C_4$ alkynylsulfinyl, $C_2$–$C_4$ alkynylsulfonyl, $C_1$–$C_4$ haloalkylthio, $C_1$–$C_4$ haloalkylsulfinyl, $C_1$–$C_4$ haloalkylsulfonyl, amino, $C_1$–$C_4$ alkylamino, $C_1$–$C_4$ dialkylamino, $C_1$–$C_4$ alkoxy-$C_1$–$C_4$ alkylamino, N-$C_1$–$C_4$ alkyl-N-$C_1$–$C_4$ alkoxy-$C_1$–$C_4$ alkylamino, $C_1$–$C_4$ alkoxyamino, N-$C_1$–$C_4$ alkyl-N-$C_1$–$C_4$ alkoxyamino, $C_1$–$C_4$ alkylcarbonylamino, N-$C_1$–$C_4$ alkyl-N-$C_1$–$C_4$ alkylcarbonylamino, $C_1$–$C_4$ alkoxycarbonylamino, N-$C_1$–alkyl-N-$C_1$–$C_4$ alkoxycarbonylamino, $C_1$–$C_4$ alkylsulfonylamino, N-$C_1$–$C_4$ alkyl-N-$C_1$–$C_4$ alkylsulfonylamino, aminosulfonyl, $C_1$–$C_4$ alkylaminosulfonyl, $C_1$–$C_4$ alkylthio-$C_1$–$C_4$ alkoxy, $C_1$–$C_4$ alkylsulfinyl-$C_1$–$C_4$ alkoxy or $C_1$–$C_4$ alkylsulfonyl-$C_1$–$C_4$ alkoxy.

5. A herbicidal composition comprising a herbicidally effective amount of a substituted bicycloheptanedione derivative according to claim 4.

6. A substituted bicycloheptanedione derivative of claim 4 having the formula:

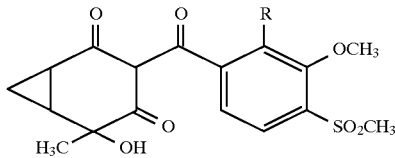

wherein R is Cl or $CH_3$.

7. A substituted bicycloheptanedione derivative of claim 4 having the formula:

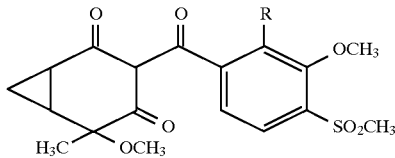

wherein R is Cl or $CH_3$.

8. A substituted bicycloheptanedione derivative of claim 4 having the formula:

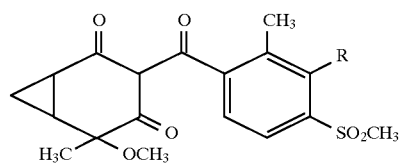

wherein R is Br or $OCHF_2$.

9. A substituted bicycloheptanedione derivative of claim 4 having the formula:

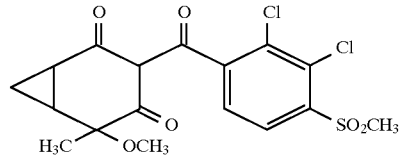

10. A substituted bicycloheptanedione derivative of claim 4 having the formula:

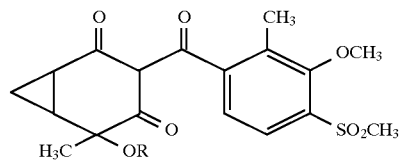

wherein R is $C_2H_5$, $nC_3H_7^n$, $^{i}C_3H_7$, $CH_2C$=CH or CHO.

11. A substituted bicycloheptanedione derivative of claim 4 having the formula:

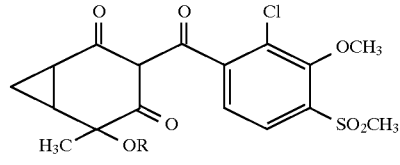

wherein R is $C_2H_5$, $CH_2CF_3$ or $C_3H_7^i$.

* * * * *